(12) United States Patent
Guo et al.

(10) Patent No.: US 12,016,717 B2
(45) Date of Patent: Jun. 25, 2024

(54) CT IMAGE GENERATION METHOD AND APPARATUS, COMPUTER DEVICE, AND COMPUTER-READABLE STORAGE MEDIUM

(71) Applicant: Tencent Technology (Shenzhen) Company Limited, Guangdong (CN)

(72) Inventors: Heng Guo, Shenzhen (CN); Xingde Ying, Shenzhen (CN); Kai Ma, Shenzhen (CN); Yefeng Zheng, Shenzhen (CN)

(73) Assignee: Tencent Technology (Shenzhen) Company Limited, Shenzhen (CN)

( * ) Notice: Subject to any disclaimer, the term of this patent is extended or adjusted under 35 U.S.C. 154(b) by 572 days.

(21) Appl. No.: 17/246,339

(22) Filed: Apr. 30, 2021

(65) Prior Publication Data

US 2021/0251590 A1  Aug. 19, 2021

Related U.S. Application Data

(63) Continuation of application No. PCT/CN2020/072393, filed on Jan. 16, 2020.

(30) Foreign Application Priority Data

Jan. 30, 2019 (CN) .......................... 201910093446.6

(51) Int. Cl.
*A61B 6/00* (2024.01)
*A61B 6/46* (2024.01)
*G06T 9/00* (2006.01)

(52) U.S. Cl.
CPC .......... *A61B 6/5223* (2013.01); *A61B 6/466* (2013.01); *A61B 6/5229* (2013.01); *G06T 9/002* (2013.01)

(58) Field of Classification Search
CPC ..... A61B 6/5223; A61B 6/466; A61B 6/5229; A61B 6/5205; G06T 9/002; G06T 11/006; G06T 2211/436; G06T 2211/441
(Continued)

(56) References Cited

U.S. PATENT DOCUMENTS

| 10,709,394 | B2 | 7/2020 | Zhou et al. |
| 2003/0078500 | A1* | 4/2003 | Evron ............... G06T 19/20 600/443 |

(Continued)

FOREIGN PATENT DOCUMENTS

| CN | 103854270 A | 6/2014 |
| CN | 106204511 A | 12/2016 |

(Continued)

OTHER PUBLICATIONS

Chen, Chih-Chia et al., "Reconstruction of the Spine Structure with Bi-planar X-ray Images Using the Generative Adversarial Network", International Forum on Medical Imaging in Asia, SPIE vol. 11050, Jan. 7-9, 2019, 5p, Singapore.

(Continued)

*Primary Examiner* — Juan A Torres
(74) *Attorney, Agent, or Firm* — Crowell & Moring LLP

(57) ABSTRACT

A CT image generation method and apparatus, a computer device, and a computer-readable storage medium are presented. The method includes obtaining a first X-ray image and a second X-ray image, the first X-ray image and the second X-ray image being X-ray images acquired for a target object from two orthogonal viewing angles; calling a generator to perform three-dimensional reconstruction on the first X-ray image and the second X-ray image, to obtain a three-dimensional model of the target object; and obtaining a CT image of the target object according to the three-dimensional model of the target object.

20 Claims, 13 Drawing Sheets

(58) Field of Classification Search
USPC .................................................. 382/128
See application file for complete search history.

(56) References Cited

U.S. PATENT DOCUMENTS

| | | | |
|---|---|---|---|
| 2019/0012581 A1 | 1/2019 | Honkala et al. | |
| 2019/0216409 A1* | 7/2019 | Zhou | A61B 6/032 |

FOREIGN PATENT DOCUMENTS

| | | |
|---|---|---|
| CN | 106952239 A | 7/2017 |
| CN | 107680158 A | 2/2018 |
| CN | 107798697 A | 3/2018 |
| CN | 108805977 A | 11/2018 |
| CN | 108876907 A | 11/2018 |
| CN | 109166087 A | 1/2019 |
| CN | 109166130 A | 1/2019 |
| CN | 109745062 A | 5/2019 |
| CN | 110047128 A | 7/2019 |
| JP | 2004-513673 A | 5/2004 |
| JP | 2016-159116 A | 9/2016 |
| WO | WO 2020/156195 A1 | 8/2020 |

OTHER PUBLICATIONS

Extended European Search Report for European patent application No. 20749748.8 dated Feb. 17, 2022, 7p.
Notice of Reasons for Refusal for Japanese patent application No. 2021-521978, dated Apr. 4, 2020, 4p, in Japanese language.
English language translation of Notice of Reasons for Refusal for Japanese patent application No. 2021-521978, Apr. 4, 2020, 4p.
Gu, Jawook et al., "Multi-Scale Wavelet Domain Residual Learning for Limited-Angle CT Reconstruction", *Korea Advanced Institute of Science and Technology*, arXiv:1703.01382v1, Mar. 4, 2017, 5p, Korea.
International Search Report and Written Opinion for priority international application No. PCT/CN2020/072393, dated Apr. 16, 2020, 11p, in Chinese language.
English language translation of International Search Report for priority international application No. PCT/CN2020/072393, dated Apr. 16, 2020, 3p.
Henzler, Philipp et al.; "Single-image Tomography: 3D Volumes from 2D Cranial X-Rays"; The Eurographics Association Computer Graphics Forum; V37, No. 2, Nov. 28, 2018; 12p.
Sinha, Ashish et al.; "GA-GAN: CT reconstruction from Biplanar DRRs using GAN with Guided Attention"; $33^{rd}$ Conference on Neural Information Processing Systems; V2, Oct. 13, 2019; 4p.
Ying, Xingde et al.; "X2CT-GAN: Reconstructing CT from Biplanar X-Rays with Generative Adversarial Network"; 2019; IEEE/CVF Conference on Computer Vision and Pattern Recognition (CVPR); Jan. 9, 2020; pp. 10619-10628.
Second Search Report and Written Opinion for Chinese application No. CN 201910093446.6 dated Sep. 23, 2019, 5p, in Chinese language.
First Search Report and Written Opinion for Chinese application No. CN 201910093446.6 dated Jul. 16, 2019; 9p; in Chinese language.
Concise Explanation of Relevancy for the First and Second Search Reports and Written Opinions for Chinese Office Action and Search Report for Chinese application No. CN 201910093446.6, 2p, Sep. 23, 2019.

\* cited by examiner

CT IMAGE GENERATION METHOD AND APPARATUS, COMPUTER DEVICE, AND COMPUTER-READABLE STORAGE MEDIUM

RELATED APPLICATIONS

This application is a continuation of PCT Patent Application No. PCT/CN2020/072393, entitled "CT IMAGE GENERATION METHOD AND APPARATUS, COMPUTER DEVICE AND COMPUTER-READABLE STORAGE MEDIUM" and filed with the China National Intellectual Property Administration on Jan. 16, 2020, which claims priority to Chinese Patent Application No. 201910093446.6, entitled "CT IMAGE GENERATION METHOD AND APPARATUS, DEVICE, AND STORAGE MEDIUM" and filed with the China National Intellectual Property Administration on Jan. 30, 2019. The above applications are incorporated herein by reference in their entireties.

TECHNICAL FIELD

Embodiments of this disclosure relate to the field of computer programs, and in particular, to a CT image generation method and apparatus, a computer device, and a computer-readable storage medium.

BACKGROUND

Computed tomography (CT) can assist a doctor in making a more precise diagnosis by providing three-dimensional structural information inside the body of a patient.

In the related art, a CT scanner scans a layer with a certain thickness of a specific part of a human body by using X-ray beams (ultrasound waves or y-rays). A detector receives X-rays passing through the layer. After converted into visible light, the X-rays are then converted into electrical signals through photoelectric conversion, and the electrical signals are converted into digital signals by using an analog/digital converter. The digital signals are inputted into a computer for processing to obtain a plurality of layers of CT images.

However, compared with X-ray films, a CT scanner brings more radiation hazards to a patient.

SUMMARY

According to various embodiments of this disclosure, a CT image generation method and apparatus, a computer device, and a computer-readable storage medium are provided.

A Computed Tomography (CT) image generation method is provided, performed by a computer, the method including:

obtaining a first X-ray image and a second X-ray image, the first X-ray film and the second X-ray image being X-ray images acquired for a target object from two orthogonal viewing angles;

performing, by using a generator, three-dimensional reconstruction based on the first X-ray image and the second X-ray image, to obtain a three-dimensional model of the target object; and obtaining a CT image of the target object according to the three-dimensional model of the target object.

A CT image generation apparatus is provided, including:

an obtaining module, configured to obtain a first X-ray film and a second X-ray film, the first X-ray film and the second X-ray film being X-ray films acquired for a target object from two orthogonal viewing angles;

a generation module, configured to perform three-dimensional reconstruction on the first X-ray film and the second X-ray film, to obtain a three-dimensional model of the target object; and an output module, configured to obtain a CT image of the target object according to the three-dimensional model of the target object.

A three-dimensional image synthetic method is provided, performed by a computer device, the method including:

obtaining a first cross-sectional image and a second cross-sectional image, the first cross-sectional image and the second cross-sectional image being images obtained by sectioning a target object by using two orthogonal cross sections;

obtaining an encoder and a decoder, the encoder including a first encoding unit and a second encoding unit, and the decoder including a first decoding unit, a second decoding unit, and a fusion decoding unit;

performing, by using the first encoding unit, two-dimensional encoding on the first cross-sectional image, to obtain first encoding information;

decoding, by the first decoding unit, the first encoding information, to obtain first decoding information;

performing, by using the second encoding unit, two-dimensional encoding on the second cross-sectional image, to obtain second encoding information;

decoding, by the second decoding unit, the second encoding information, to obtain second decoding information; and performing, by using the fusion decoding unit, three-dimensional fusion by using the first decoding information and the second decoding information as data of different viewing angles in a three-dimensional space, to obtain a three-dimensional image of the target object.

A three-dimensional image synthetic apparatus, including:

an obtaining module, configured to obtain a first cross-sectional image and a second cross-sectional image, the first cross-sectional image and the second cross-sectional image being images obtained by sectioning a target object by using two orthogonal cross sections; and the obtaining module being further configured to obtain an encoder and a decoder, the encoder including a first encoding unit and a second encoding unit, and the decoder including a first decoding unit, a second decoding unit, and a fusion decoding unit, the first encoding unit being configured to perform two-dimensional encoding on the first cross-sectional image, to obtain first encoding information;

the first decoding unit being configured to decode the first encoding information, to obtain first decoding information;

the second encoding unit being configured to perform two-dimensional encoding on the second cross-sectional image, to obtain second encoding information;

the second decoding unit being configured to decode the second encoding information, to obtain second decoding information; and the fusion decoding unit being configured to perform three-dimensional fusion by using the first decoding information and the second decoding information as data of different viewing angles in a three-dimensional space, to obtain a three-dimensional image of the target object.

A three-dimensional image processing apparatus, comprising:

an encoder, configured to perform, in parallel, two-dimensional encoding on a first cross-sectional image to obtain first encoding information and two-dimensional encoding on a second cross-sectional image to obtain second encoding information, the first cross-sectional image and the second cross-sectional image being images acquired for a target object from two orthogonal viewing angles; and a decoder in communication with the encoder and being configured to:

decode, in parallel, the first encoding information to obtain first decoding information and the second encoding information to obtain second decoding information; and perform three-dimensional fusion by using the first decoding information and the second decoding information as data of different viewing angles in a three-dimensional space to obtain a three-dimensional image of the target object.

A computer device is provided. The computer device includes a processor and a memory, the memory storing at least one program, the at least one program being loaded and executed by the processor to implement the CT image generation method or the three-dimensional image synthetic method.

A non-transitory computer-readable storage medium is provided. The storage medium stores at least one program, the at least one program being loaded and executed by a processor to implement the CT image generation method or the three-dimensional image synthetic method.

BRIEF DESCRIPTION OF THE DRAWINGS

To describe the technical solutions of the embodiments of this disclosure more clearly, the following briefly introduces the accompanying drawings required for describing the embodiments. Apparently, the accompanying drawings in the following description show only some embodiments of this disclosure, and a person of ordinary skill in the art may still derive other drawings from these accompanying drawings without creative efforts.

DESCRIPTION OF EMBODIMENTS

Figure 1:
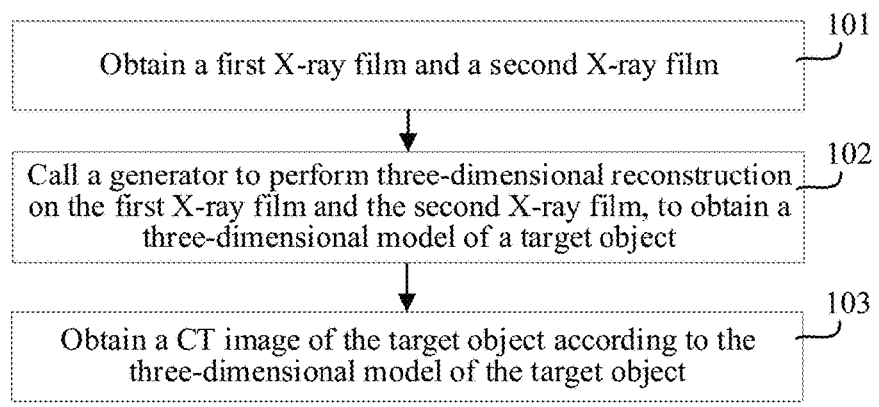
FIG. 1 is a flowchart of a CT image generation method according to an embodiment of this disclosure.

To make objectives, technical solutions, and advantages of the embodiments of this disclosure clearer, the following further describes in detail implementations of this disclosure with reference to the accompanying drawings.

Although terms such as first and second are used to describe various elements in the following description, these elements are not to be limited to these terms. These terms are merely used for distinguishing one element from another element. For example, a first user status option may be referred to as a second user status option, and similarly, a second user status option may be referred to as a first user status option without departing from the scope of the various examples. Both the first user status option and the second user status option may be user status options, and in some cases, may be independent and different user status options.

Terms used in description of the various examples in this specification are merely for describing specific examples and are not intended to impose limitations. As used in the description of the various examples and the appended claims, singular forms, "a" or "an" and "the", are intended to also include plural forms, unless the context clearly indicates otherwise. It is to be further understood that as used herein, the term "and/or" refers to and includes any and all possible combinations of one or more of the associated listed items. It is to be further understood that the terms "includes", "including", "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Based on the context, the term "if" may be interpreted as a meaning of "when" or "upon", "in response to determining", or "in response to detecting". Similarly, based on the context, the phrase "if determining" or "if detecting (a stated condition or event)" may be interpreted as a meaning of "when determining . . . ", "in response to determining . . . ", "when detecting (a stated condition or event)", or "in response to detecting . . . (a stated condition or event)".

First, several terms described in the embodiments of this disclosure are briefly introduced.

X-ray: referred to as an X-ray film, a medical image modality in a two-dimensional form. The X-ray film can clearly image the bone region and is often used as the basis for diagnosis by an orthopedist. The X-ray film in this disclosure does not necessary refer to a physical film. The term may mean a digital image made by a radiographic method.

CT image: a medical image modality in a three-dimensional form. Information included in the CT image is more abundant, but there are more radiation doses.

GAN (Generative Adversarial Network): a generation model with a capability of capturing distribution of real data, widely studied in recent years.

Generator: a component of the GAN, responsible for generating sufficiently real data.

Discriminator: a part in the GAN adversarial to the generator, and responsible for determining whether data generated by the generator is close to real data.

Digitally reconstructed radiograph (DRR): a digitally reconstructed image. In this specification, virtual X-ray films generated by using a DRR technology are used as a training dataset of the GAN.

CycleGAN: a model for implementing style transformation between two unmatched datasets.

In the medical field, a CT image can assist a doctor in making a more precise diagnosis by providing three-dimensional structural information inside the body of a patient. However, compared with X-ray films, CT not only brings more radiation hazards to the patient, but also has shortcomings of relatively high checking costs and a long checking time. Besides, because of the expensiveness of a CT scanner, it is difficult for the CT scanner to cover all medical regions. Usually, hundreds of X-ray projections covering the whole body of a patient are needed in the conventional CT reconstruction method, which is difficult to implement by a general X-ray film acquisition device.

Certain embodiments of this disclosure provide a new idea, that is, a complete three-dimensional CT image is reconstructed by merely using two orthogonal X-ray films in a GAN frame. Therefore, the embodiments of this disclosure provide a generator (or referred to as a neural network architecture), responsible for upgrading two-dimensional data (an X-ray film) to three-dimensional data (a CT image). Also, certain embodiments of this disclosure provide a method for fusing information from two viewing angles during end-to-end learning. For a region lacking of CT scanners, the method provided in certain embodiments of this disclosure provides a possibility of obtaining three-dimensional information inside a human body by using a low-cost X-ray film acquisition device.

FIG. 1 is a flowchart of a CT image generation method according to an embodiment of this disclosure. The method may be performed by a computer device. The method includes the following steps:

Step 101: Obtain a first X-ray film and a second X-ray film, the first X-ray film and the second X-ray film being X-ray films acquired for a target object from two orthogonal viewing angles.

The target object may be a target medical living body to be detected. The target object may be an animal such as a human being, a dog, or a cow, but a possibility that the target object is a plant or another object is not excluded.

Exemplarily, the first X-ray film and the second X-ray film are X-ray films acquired for a target object from two orthogonal viewing angles at two relatively close moments. In some embodiments, the statement that the viewing angles of the two X-ray films are orthogonal to each other mean that the viewing angles are orthogonal or substantially orthogonal (±5% or ±10% tolerance). So long as the CT image generated based on the X-ray films is acceptable for its purpose, the scope of the term "orthogonal" is covered by the embodiments of this disclosure.

Figure 2:
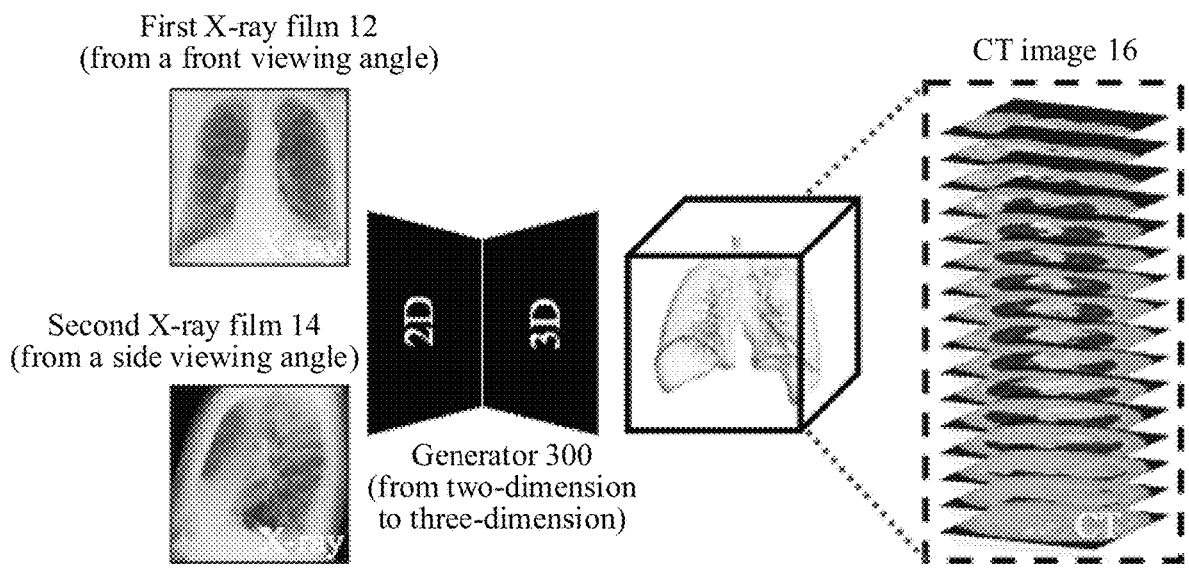
FIG. 2 is a schematic diagram of a principle of a CT image generation method according to another embodiment of this disclosure.

Referring to FIG. 2, a first X-ray film 12 is an X-ray film acquired for the target object from a front viewing angle, and a second X-ray film 14 is an X-ray film acquired for the target object from a side viewing angle.

Step 102: Call a generator to perform three-dimensional reconstruction on the first X-ray film and the second X-ray film, to obtain a three-dimensional model of the target object.

Exemplarily the generator is constructed based on a GAN. The generator includes an encoder and a decoder.

The computer device calls the encoder to separately encode the first X-ray film and the second X-ray film to obtain first encoding information and second encoding information; the computer device further calls the decoder to perform three-dimensional reconstruction decoding on the first encoding information and the second encoding information to obtain the three-dimensional model of the target object.

Step 103: Obtain a CT image of the target object according to the three-dimensional model of the target object.

Referring to FIG. 2, a generator 300 performs three-dimensional reconstruction on the first X-ray film 12 and the second X-ray film 14 to obtain a three-dimensional model of the target object. The computer device generates a CT image 16 of the target object according to the three-dimensional model.

Usually, the CT image 16 includes various layers of two-dimensional images. Based on the three-dimensional model by reconstructing the target object, the CT image 16 of the target object may be generated.

Based on the above, in the method provided in this embodiment, two orthogonal X-ray films are inputted into a generator, and the generator reconstructs a CT image of a target object through three-dimensional reconstruction. In this way, a three-dimensional medical image equivalent to or similar to an image obtained by using a CT scanner can be obtained by performing merely two times of X-ray film scanning in a two-dimensional form by an X-ray film device, reducing radiation hazards to the target object, saving checking costs of the target object, and shortening a checking time of the target object.

Generator Structure

Figure 3:
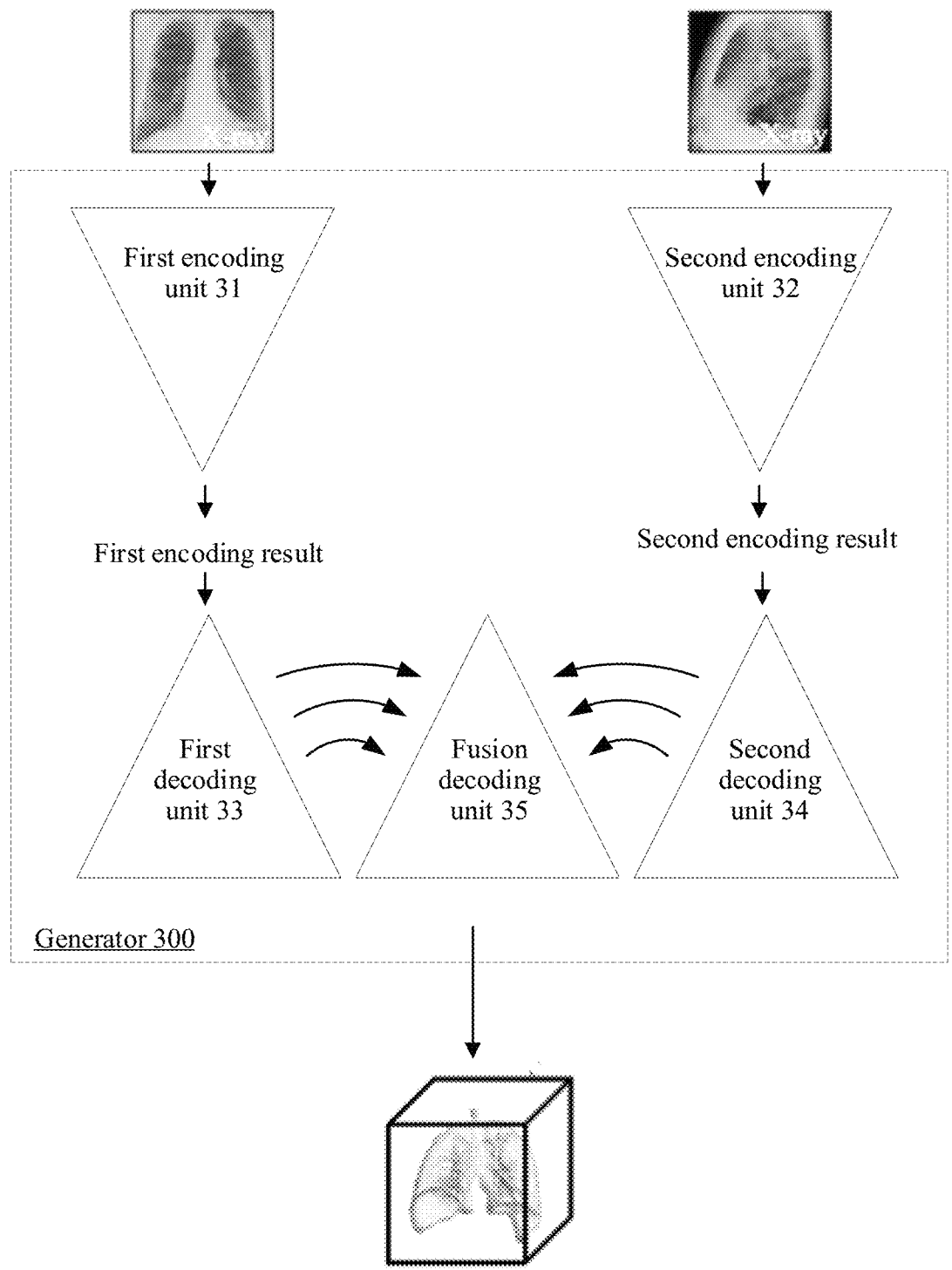
FIG. 3 is a structural block diagram of a generator according to an embodiment of this disclosure.

The foregoing generator 300 may be a generator trained based on a GAN. The generator is endowed with a capability of performing three-dimensional reconstruction on two-dimensional images from two orthogonal viewing angles to obtain a three-dimensional model. FIG. 3 is a structural block diagram of a generator 300 according to an embodiment of this disclosure. The generator 300 includes an encoder and a decoder.

The encoder includes a first encoding unit 31 and a second encoding unit 32. Exemplarily, a network structure of the first encoding unit 31 is the same as that of the second encoding unit 32.

The computer device calls the first encoding unit 31 to perform two-dimensional encoding on the first X-ray film to obtain the first encoding information and calls the second encoding unit 32 to perform two-dimensional encoding on the second X-ray film to obtain the second encoding information.

The decoder includes a first decoding unit 33, a second decoding unit 34, and a fusion decoding unit 35. Exemplarily, a network structure of the first decoding unit 33 is the same as that of the second decoding unit 34.

The computer device calls the first decoding unit 33 to decode the first encoding information to obtain first decoding information, calls the second decoding unit 34 to decode the second encoding information to obtain second decoding information, and calls the fusion decoding unit 35 to perform three-dimensional fusion by using the first decoding information and the second decoding information as data of different viewing angles in a three-dimensional space to obtain the three-dimensional model of the target object.

That is, the fusion decoding unit 35 fuses decoding information with two different viewing angles of the first decoding unit 33 and the second decoding unit 34 to obtain the three-dimensional model of the target object.

Figure 4:
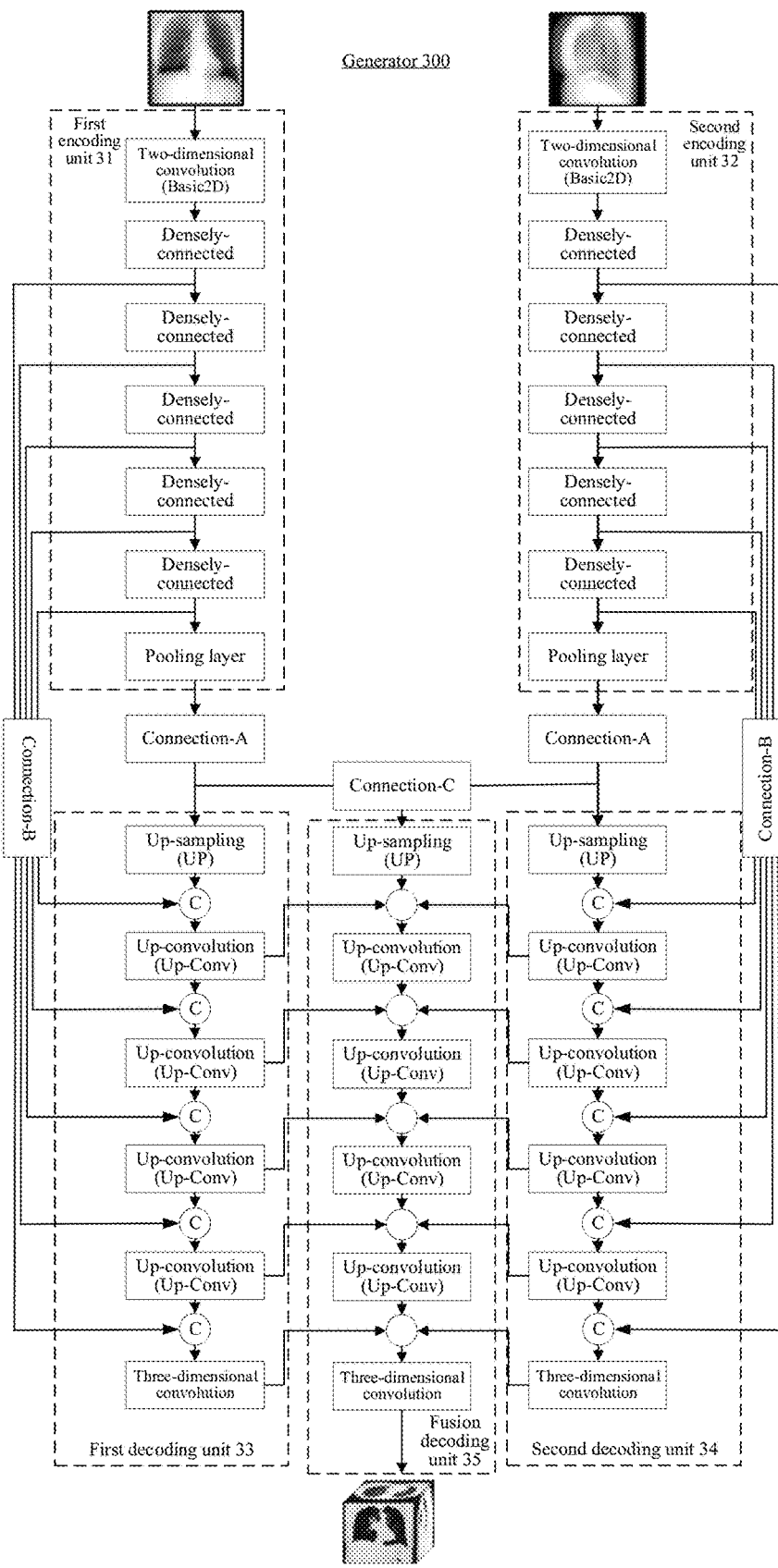
FIG. 4 is a structural block diagram of a generator according to another embodiment of this disclosure.

Exemplarily, the foregoing generator 300 is named as X2CT-CNN. The first encoding unit 31 and the first decoding unit 33 may be considered as belonging to one codec network. The second encoding unit 32 and the second decoding unit 34 may be considered as belonging to another codec network. The generator 300 encodes and decodes an input of a front view and an input of a side view in parallel by using two codec networks with the same structure and performs three-dimensional reconstruction by using the fusion decoding unit 35 in the middle. The codec network aims to learn a mapping relationship between an X-ray film and a CT image. The fusion decoding unit 35 in the middle aims to reconstruct a corresponding three-dimensional CT structure by using feature information from the two codec networks. To complete the data conversion, a schematic design shown in FIG. 4 is further used for the generator 300.

The first encoding unit 31 includes n+2 encoding layers: a two-dimensional convolutional layer, n cascaded densely-connected layer, and a pooling layer. The two-dimensional convolutional layer is connected to the first densely-connected layer, and the $n^{th}$ densely-connected layer is connected to the pooling layer. n is a positive integer greater than 1.

A structure of the second encoding unit 32 is the same as that of the first encoding unit 31.

The first encoding unit 31 is further connected to the first decoding unit 33 through a first connection-A. The first connection-A is used for converting the first encoding information from the two-dimensional form to a three-dimensional form. The second encoding unit 32 is further connected to the second decoding unit 34 through a second connection-A. The second connection-A is used for converting the second encoding information from the two-dimensional form to a three-dimensional form. The connection-A is a connection implemented based on a fully connected layer.

The first decoding unit 33 includes n+2 decoding layers: an up-sampling (UP) layer, n cascaded up-convolutional (UP-Conv) layers, and a three-dimensional convolutional layer. The up-sampling layer is connected to the first up-convolutional layer, and the $n^{th}$ up-convolutional layer is connected to the three-dimensional convolutional layer. The foregoing layers form the n+2 decoding layers. Exemplarily, the first decoding unit 33 further includes n connections-C. Each connection-C includes two input terminals and an output terminal. A first input terminal of an $i^{th}$ connection-C is connected to an output terminal of an $i^{th}$ decoding layer in the first decoding unit 33, a second input terminal of the $i^{th}$ connection-C is connected to an output terminal of an (i+1)$^{th}$ encoding layer in the first encoding unit 31, and an output terminal of the $i^{th}$ connection-C is connected to an input terminal of an (i+1)$^{th}$ decoding layer in the first decoding unit 33.

Exemplarily, the second input terminal of the $i^{th}$ connection-C is further connected to an output terminal of an (i+1)$^{th}$ encoding layer in the first encoding unit 31 through a connection-B. The connection-B is used for converting two-dimensional encoding information outputted by an encoding layer into three-dimensional encoding information. The connection-C is used for performing weighted summation on three-dimensional decoding information inputted from the first input terminal and three-dimensional encoding information inputted from the second input terminal, to output three-dimensional decoding information for a next decoding layer.

A structure of the second decoding unit 34 is the same as that of the first decoding unit 33. Details are not repeated.

Figure 5A:
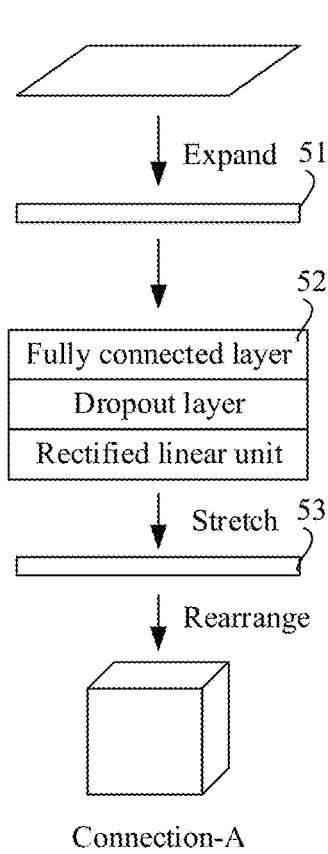
FIGS. 5A to 5C are schematic structural diagrams of a connection-A, a connection-B, and a connection-C according to an embodiment of this disclosure.
Figures 5B, 5C:
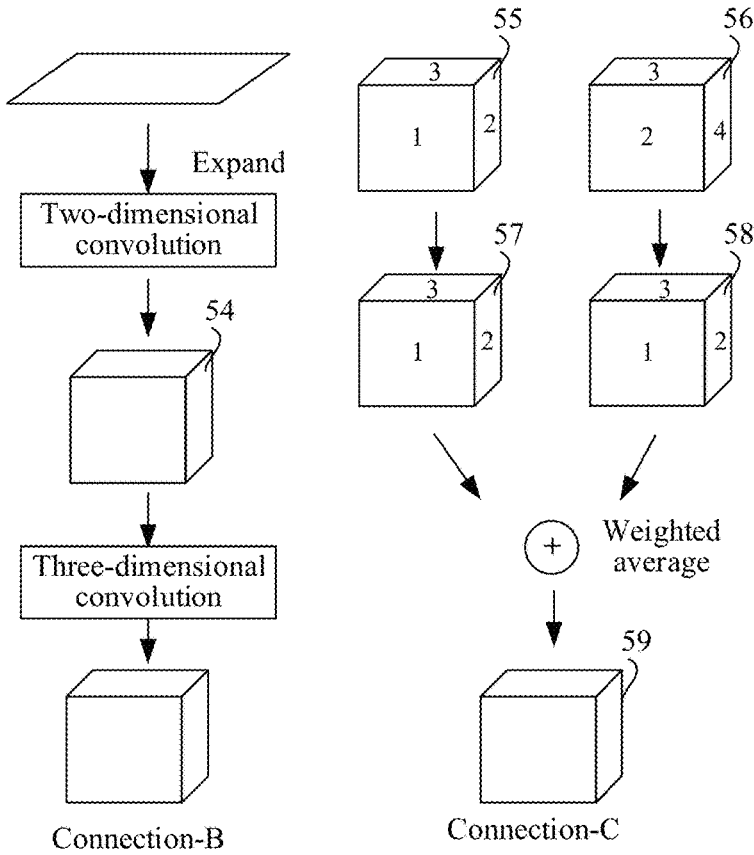

FIGS. 5A to 5C are schematic structural diagrams of the foregoing three types of connections.

FIG. 5A is a schematic structural diagram of the connection-A. The connection-A is used for expanding encoding information in a two-dimensional form into a first one-dimensional vector 51, stretching the first one-dimensional vector 51 into a second one-dimensional vector 53 by using a fully-connected module 52, and rearranging the second one-dimensional vector 53 into encoding information in a three-dimensional form. Exemplarily, the fully-connected module includes a fully connected (FC) layer, a Dropout layer, and a rectified linear unit (ReLU) layer.

FIG. 5B is a schematic structural diagram of the connection-B. The connection-B is used for expanding two-dimensional encoding information outputted by the ith encoding layer into m layers in a vertical dimension, and determining expanded two-dimensional encoding information of m layers as the three-dimensional encoding information, m being a positive integer. Exemplarily, the connection-B includes a two-dimensional convolutional layer and a three-dimensional convolutional layer. The connection-B converts a quantity of channels of a two-dimensional feature into a quantity of channels of a three-dimensional feature 54 in a corresponding decoding layer through the two-dimensional convolutional layer, adds a vertical dimension which is perpendicular to the two-dimensional encoding information for the two-dimensional feature with a changed quantity of channels, then obtains m layers of two-dimensional encoding information through duplication on the vertical dimension to enable the two-dimensional encoding information to be changed to pseudo three-dimensional encoding information, and then encodes the pseudo three-dimensional encoding information again through the three-dimensional convolutional layer.

The above skip connection bridges the two-dimensional encoding information and the three-dimensional encoding information in a more natural manner and enables some low-level two-dimensional encoding information closely relevant to an X-ray film to fully reach an output terminal and have a direct impact. The largest benefit brought is that a strong correlation between shape and space is introduced between an input and an output.

FIG. 5C is a schematic structural diagram of the connection-C. The connection-C is used for performing, after transforming three-dimensional encoding/decoding information inputted from the first input terminal and three-dimensional encoding/decoding information inputted from the second input terminal into the same three-dimensional space, weighted summation on the two pieces of three-dimensional encoding/decoding information in the three-dimensional space, which is outputted as an input of a next decoding layer. Schematically, the three-dimensional encoding/decoding information 55 inputted from the first input terminal is obtained by encoding/decoding the first X-ray film acquired from a front viewing angle, and the three-dimensional encoding/decoding information 56 inputted from the second input terminal is obtained by encoding/decoding the second X-ray film acquired from a side viewing angle, so viewing angles of the two pieces of three-dimensional encoding/decoding information are different. Therefore, one or two pieces of three-dimensional encoding/decoding information are converted first to enable two pieces of three-dimensional encoding/decoding information 57 and 58 to be in the same three-dimensional space, and weighted averaging is then performed on the two pieces of three-dimensional encoding/decoding information 57 and 58 in the three-dimensional space to obtain synthesized three-dimensional decoding information 59 as an input of a next decoding layer.

The fusion decoding unit 35 includes n+2 fusion decoding layers, that is, an up-sampling layer, n cascaded up-convolutional layers, and a three-dimensional convolutional layer. An output terminal of the up-sampling layer is connected to the first up-convolutional layer, and the $n^{th}$ up-convolutional layer is connected to the three-dimensional convolutional layer.

Exemplarily, the fusion decoding unit 35 further includes a connection-C. A first input terminal of the connection-C is connected to an input terminal of the first decoding unit 33, a second input terminal of the connection-C is connected to an input terminal of the second decoding unit 34, and an output terminal of the connection-C is connected to an input terminal of the up-sampling layer. In the fusion decoding unit 35, the connection-C is used for performing weighted summation on three-dimensional encoding information inputted from the first input terminal and three-dimensional encoding information inputted from the second input terminal, and using an outputted result as an input of a next fusion decoding layer.

Figure 6:
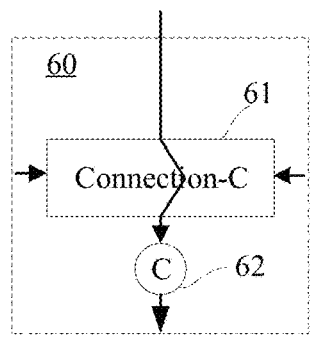
FIG. 6 is a schematic structural diagram of a compound connection-C according to an embodiment of this disclosure.

Exemplarily, the fusion decoding unit 35 further includes n compound connections-C, as shown in FIG. 6. Each compound connection-C 60 includes a first connection-C 61 and a second connection-C 62. A first input terminal of an $i^{th}$ first connection-C 61 is connected to an output terminal of an $(i+1)^{th}$ decoding layer in the first decoding unit 33, a second input terminal of the $i^{th}$ first connection-C 61 is connected to an output terminal of an $(i+1)^{th}$ decoding layer in the second decoding unit 34, an output terminal of the $i^{th}$ first connection-C 61 is connected to a first input terminal of the $i^{th}$ second connection-C 62, a second input terminal of the $i^{th}$ second connection-C 62 is connected to an output terminal of an $i^{th}$ fusion decoding layer in the fusion decoding unit 35, and an output terminal of the $i^{th}$ second connection-C is connected to an input terminal of an $(i+1)^{th}$ fusion decoding layer in the fusion decoding unit 35.

The following introduces some embodiments of the generator 300:

(1) A densely-connected design for an encoder.

Each densely-connected (Dense) layer is composed of a down-sampling block (Down), a densely-connected block (Dense Block), and a channel compression block (Compress). The down-sampling block is configured to perform a two-dimensional convolutional operation with a stride being 2. The channel compression block is configured to reduce a quantity of output channels to half.

The densely-connected layer has great advantages in a feature extraction process, for example, alleviating the vanishing gradient problem in the deep web and being beneficial to reuse of multi-level features, thereby extracting sufficient information from an X-ray film in a two-dimensional form.

(2) A bridging module between a two-dimensional feature and a three-dimensional feature.

In some codec networks, encoders are usually connected to decoders in a convolutional manner. There is no problem with such a manner in a purely two-dimensional network or a purely three-dimensional network. However, the particularity of the problem to be resolved in the embodiments of this disclosure lies in processing of data with different dimensions. Therefore, a new module is needed to bridge two pieces of information in different dimensions. For architecture designs for a neural network in recent years, a convolutional layer has replaced a fully connected layer in most cases for the reason that the fully connected layer has a shortcoming of a massive quantity of parameters. However, in many neural network architectures, connections between information in different dimensions are still processed in a large quantity of fully-connected manners. In the work related to a GAN, a dimension increasing process from one-dimensional noise to a two-dimensional image in most case is also completed by using a fully connected layer, which well shows that the fully connected layer still has a value in specific scenarios. In this embodiment of this disclosure, the fully connected layer is expanded into a new connection module named connection-A (see FIG. 5A). The connection-A is responsible for connecting a two-dimensional encoder to a three-dimensional decoder at an intermediate node of the generator. The connection manner may mess up spatial arrangement or a relationship between adjacent positions of features to some extent, and the problem of the massive quantity of parameters in the fully connected layer still cannot be avoided, resulting in that the connection manner cannot be generalized to a relatively shallow layer in the generator. To resolve the problems, and to make the skip connection work in the generator provided in this embodiment of this disclosure, a connection-B (see FIG. 5B) comes into being.

The connection-A implements a transition from a two-dimensional feature to a three-dimensional feature by using a manner of a fully connected layer. After multi-channel encoding information in a two-dimensional form is obtained in the last layer of the encoder, the connection-A first expands the encoding information into a one-dimensional vector 51, and then stretches the vector into a longer one-dimensional vector 53 (the length can be calculated by an expected size of a three-dimensional feature), and finally rearranges the longer one-dimensional vector 53 into a three-dimensional feature. Because by using the connection manner, much information in a two-dimensional space may be lost, the connection-A is only used between the last layer of the encoder and the first layer of the decoder in this embodiment of this disclosure.

Other layers in the generator use the skip connection, that is, the connection-B, to promote direct flow of information about the two-dimensional feature in the encoder into a three-dimensional feature layer of the decoder.

(3) Fusion of information from two viewing angles.

Information about a three-dimensional object from a side viewing angle cannot be captured by using a two-dimensional projection from a front viewing angle, and vice versa. Therefore, in this disclosure, a more precise reconstruction result is generated by using complementary information about X-ray films acquired from two viewing angles in two orthogonal directions. Two codec networks with the same structure independently encode and decode in parallel an input of a front view and an input of a side view. A fusion decoding unit between the two codec networks is responsible for fusion of information from two viewing angles. In this embodiment of this disclosure, assuming that a time interval between acquisition of the two X-ray films from two orthogonal viewing angles may be negligible, which means no data drift caused by movement of the body of a patient, weighted averaging may be directly performed after the information from two viewing angles is converted into the same three-dimensional coordinate space, as shown in FIG. 5C. Any spatial discrepancy between outputs of encoders from two viewing angles can be captured by the fusion decoding unit, and the error information is then transmitted back to respective codec networks through back propagation.

Figure 7:
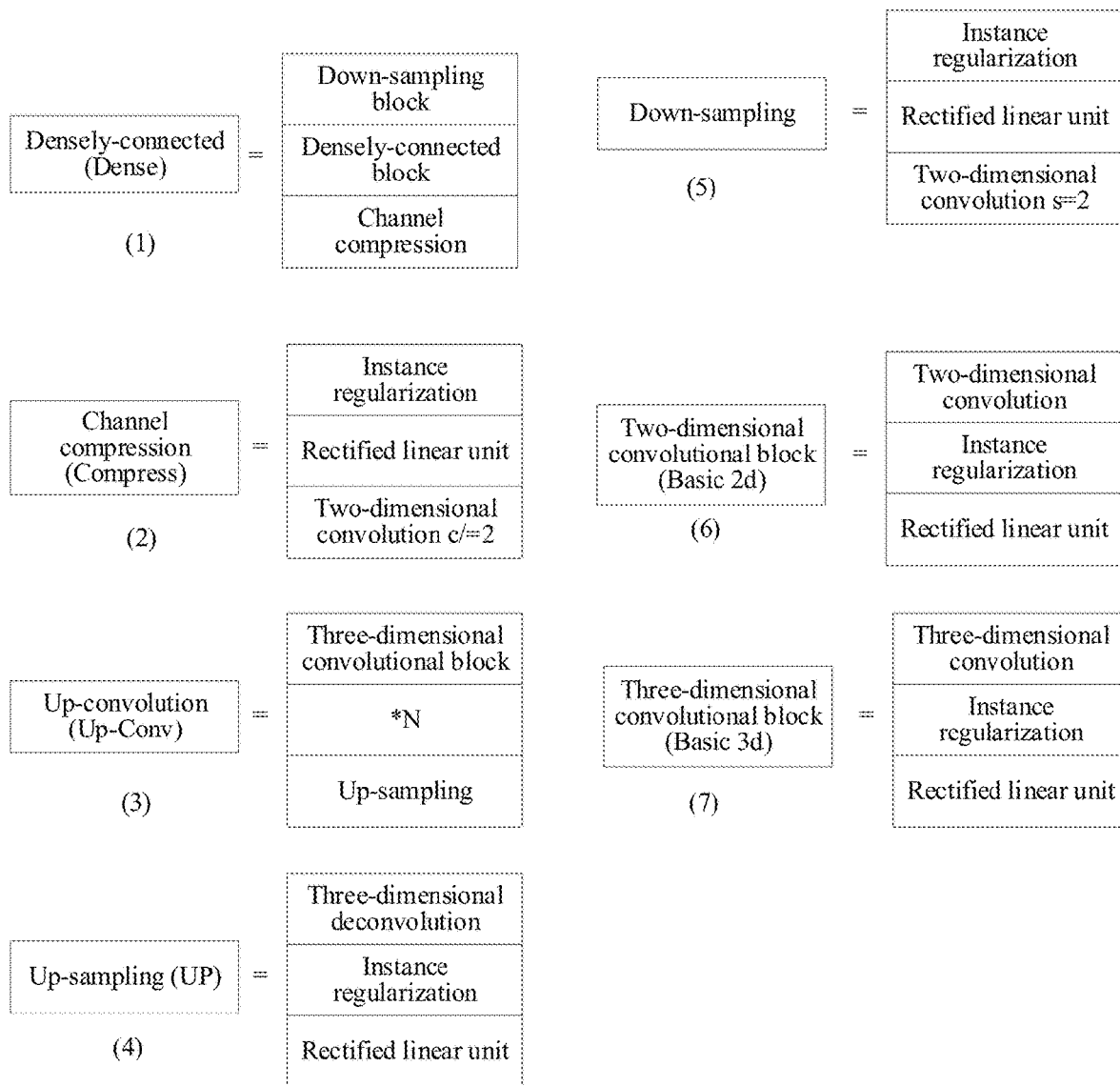
FIG. 7 is a block diagram of a neural network module according to an embodiment of this disclosure.

In Table 1 and FIG. 7, detailed setting situations of parameters in each layer of a backbone network of the generator 300 are summarized, where s=2 in the densely-connected layer means that the stride of down sampling convolution is 2. Correspondingly, sf=2 in the up-sampling layer means that the stride of transposed convolution is 2. An input of each up-convolutional layer is combination of a feature obtained through up-sampling and a feature transferred through skip connection. Therefore, one layer of convolution is used first to compress a quantity of channels. Schematically, an input of the network is a 128×128 X-ray film, and an output is a 128×128×128 CT image.

TABLE 1

Detailed network setting of generator

| Network layer name | Set parameter | Output size |
|---|---|---|
| Two-dimensional convolutional block (Basic2d) | [7 × 7, 64] | 128 × 128 |
| Densely-connected layer 0 (Dense_0) | IN, ReLU, [3 × 3, 64, s = 2]<br>IN, ReLU, [1 × 1, 128]   ×6<br>IN, ReLU, [3 × 3, 32]<br>IN, ReLU, [1 × 1, 128] | 64 × 64 |
| Densely-connected layer 1 (Dense_1) | IN, ReLU, [3 × 3, 128, s = 2]<br>IN, ReLU, [1 × 1, 128]   ×12<br>IN, ReLU, [3 × 3, 32]<br>IN, ReLU, [1 × 1, 256] | 32 × 32 |
| Densely-connected layer 2 (Dense_2) | IN, ReLU, [3 × 3, 256, s = 2]<br>IN, ReLU, [1 × 1, 128]   ×24<br>IN, ReLU, [3 × 3, 32]<br>IN, ReLU, [1 × 1, 512] | 16 × 16 |
| Densely-connected layer 3 (Dense_3) | IN, ReLU, [3 × 3, 512, s = 2]<br>IN, ReLU, [1 × 1, 128]<br>IN, ReLU, [3 × 3, 32]   ×16<br>IN, ReLU, [1 × 1, 512] | 8 × 8 |
| Densely-connected layer 4 (Dense_4) | IN, ReLU, [3 × 3, 512, s = 2]<br>IN, ReLU, [1 × 1, 128]   ×6<br>IN, ReLU, [3 × 3, 32] | 4 × 4 |
| Pooling layer (Pooling) | Average Pooling -> 704 | 1 × 1 |
| Connection-A | FC, 704 -> 16384 (256 × $4^3$) | 4 × 4 × 4 |
| Up-sampling layer (Up) | [3 × 3 × 3, 128, sf = 2], IN, ReLU | 8 × 8 × 8 |
| Up-convolutional layer 0 (Up_Conv_0) | [3 × 3 × 3, 128], IN, ReLU<br>[3 × 3 × 3, 128] × 2, IN, ReLU<br>[3 × 3 × 3, 64, sf = 2], IN, ReLU | 16 × 16 × 16 |
| Up-convolutional layer 1 (Up_Conv_1) | [3 × 3 × 3, 64], IN, ReLU<br>[3 × 3 × 3, 64] × 2, IN, ReLU<br>[3 × 3 × 3, 32, sf = 2], IN, ReLU | 32 × 32 × 32 |
| Up-convolutional layer 2 (Up_Conv_2) | [3 × 3 × 3, 32], IN, ReLU<br>[3 × 3 × 3, 32] × 2, IN, ReLU<br>[3 × 3 × 3, 16, sf = 2], IN, ReLU | 64 × 64 × 64 |
| Up-convolutional layer 3 (Up_Conv_3) | [3 × 3 × 3, 16], IN, ReLU<br>[3 × 3 × 3, 16] × 2, IN, ReLU<br>[3 × 3 × 3, 16, sf = 2], IN, ReLU | 128 × 128 × 128 |
| Three-dimensional convolutional block (Basic3d) | [7 × 7 × 7, 1], ReLU | 128 × 128 × 128 |

In Table 1, sf represents a stride, IN represents instance regularization, and ReLU represents a rectified linear unit.

As shown in (1) to (7) in FIG. 7, the densely-connected (Dense) layer includes a down-sampling block, a densely-connected block, and a channel compression block that are sequentially connected; channel compression (Compress) includes instance regularization, a rectified linear unit, and two-dimensional convolution; up-convolution (Up-Conv) includes a three-dimensional convolutional block, a *N block, and up-sampling; up-sampling (UP) includes three-dimensional deconvolution, instance regularization, and a rectified linear unit; down-sampling includes instance regularization, a rectified linear unit, and two-dimensional convolution with a stride being 2; the two-dimensional convolutional block includes two-dimensional convolution, instance regularization, and a rectified linear unit; and the three-dimensional convolutional block includes three-dimensional convolution, instance regularization and a rectified linear unit.

The foregoing network parameter setting is merely described to provide an example. Sizes of an input image and an output image are not limited in this embodiment of this disclosure. When the input image and the output image are in other sizes, setting of the neural network architecture may be adjusted correspondingly.

Training of Generator.

Figure 8:
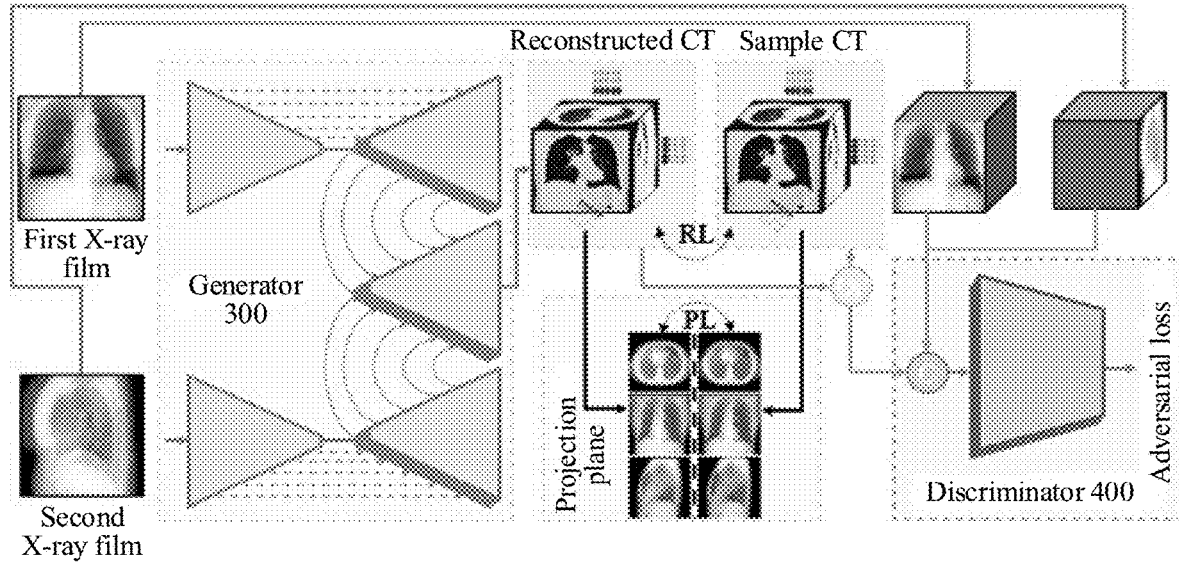
FIG. 8 is a block diagram of a generative adversarial network (GAN) according to an embodiment of this disclosure.

The foregoing generator 300 is trained based on a GAN. FIG. 8 shows an overall structure of X2CT-GAN. The GAN includes the generator 300 and a discriminator 400. Inputs of the generator 300 is an orthogonal first X-ray film (front view) and second X-ray film (side view). An output of the generator 300 is a reconstructed three-dimensional model, reconstructed CT in short. Sample CT is provided in a training dataset. The discriminator 400 is configured to distinguish an adversarial loss between the reconstructed CT and the sample CT. A smaller adversarial loss indicates a better reconstruction effect by the generator 300.

Different from a case in which a conventional GAN merely uses an adversarial loss as a loss function of a generator, a loss function of the generator provided in the embodiments of this disclosure may use any one of the following forms:

an adversarial loss; or the adversarial loss and a reconstruction loss (RL); or the adversarial loss and a projection loss (PL); or the adversarial loss, the reconstruction loss (RL), and the projection loss (PL), where the adversarial loss is used for representing a semantic loss between the three-dimensional model reconstructed by the generator and the sample CT image, the reconstruction loss is used for representing a pixel-level discrepancy loss between the three-dimensional model reconstructed by the generator and the sample CT image, and the projection loss is used for representing a discrepancy loss between the three-dimensional model reconstructed by the generator and the sample CT image on at least one projection plane.

An example in which three types of loss functions, respectively the adversarial loss, the reconstruction loss, and the projection loss, are used simultaneously during training is used. The following describes the three types of loss functions separately:

(1) Adversarial loss.

A least squares loss is used to replace a logarithmic loss form in an original GAN, improving the training stability and the image generation quality and diversity. A least squares GAN (LSGAN) has an excellent performance in a reconstruction task. In addition, due to strict constraints of the reconstruction task, LSGAN is defined in this embodiment as:

$$\mathcal{L}_{LSGAN}(D) = \frac{1}{2}[\mathbb{E}_{y \sim p(CT)}(D(y|x) - 1)^2 + \mathbb{E}_{x \sim p(Xray)}(D(G(x)|x) - 0)^2], \quad (3\text{-}1)$$

$$\mathcal{L}_{LSGAN}(G) = \frac{1}{2}[\mathbb{E}_{x \sim p(Xray)}(D(G(x)|x) - 1)^2]$$

where x represents two inputted X-ray films from two orthogonal viewing angles, y represents corresponding CT images, D(yJx) represents a discriminator, and G(x) represents a generator.

(2) Reconstruction loss.

The adversarial loss tries to enable generated data to get closer to real data. However, in a reconstruction task having an extremely high requirement for precision, it is not enough to merely have the adversarial loss. The reason is that generally speaking, the adversarial loss is an advanced semantic loss. For example, the discriminator of the X2CT-GAN merely outputs "true" or "false". A pair of reconstructed lungs that are slightly shrunk may still seem to be true to the discriminator, but may be extremely different from an expected result. Therefore, a single adversarial loss cannot ensure the uniformity of the output result and input information in shape. In addition, although the medical image is not like a natural image which is colorful and changeful, the medical image has a higher requirement for precision. Based on such considerations, a voxel-level reconstruction loss is also added in training of the X2CT-GAN model in this specification, to impose a corresponding limit on each point in a three-dimensional space. The reconstruction loss in this specification is defined based on a mean squared error (MSE), and is as follows:

$$\mathcal{L}_{re} = \mathbb{E}_{x,y}\|y - G(x)\|_2^2 \quad (3\text{-}2)$$

where, G(x) represents a generator, and y represents a CT image.

(3) Projection loss.

The reconstruction loss imposes a detailed limit on each point in the three-dimensional space. Besides, a policy of imposing a limit on a projection in a two-dimensional space is also adopted in this embodiment of this disclosure. The idea originates from an idea that if a reconstructed CT image can perfectly coincide with a reference CT image in a three-dimensional space, two-dimensional projections thereof may also coincide, and directly imposing a limit on a projection during training may improve the reconstruction precision of a three-dimensional object. To simplify a projection operation, an orthogonal projection is used in this embodiment instead of a perspective projection. However, in another embodiment, a perspective projection may be alternatively used for expression. To enable a projection to carry more information, three projection planes are selected in this embodiment, which are respectively a cross-sectional plane, a coronal plane, and a sagittal plane. The mathematical expression form thereof is as follows:

$$\mathcal{L}_{pl} = \frac{1}{3}[\mathbb{E}_{x,y}\|P_{ax}(y) - P_{ax}(G(x))\|_1 + \quad (3\text{-}3)$$
$$\mathbb{E}_{x,y}\|P_{co}(y) - P_{co}(G(x))\|_1 + \mathbb{E}_{x,y}\|p_{sa}(y) - P_{sa}(G(x))\|_1]$$

where $P_{ax}$, $P_{co}$, and $P_{sa}$ respectively represent a cross-sectional plane, a coronal plane, and a sagittal plane.

When the adversarial loss, the reconstruction loss, and the projection loss are used simultaneously, a total loss may be calculated in a manner of weighted summation and expressed as follows:

$$D^* = \arg\min \lambda_1 \mathcal{L}_{LSGAN}(D)$$

$$G^* = \arg\min_G [\lambda_1 \mathcal{L}_{SGAN}(G) + \lambda_2 \mathcal{L}_{re} + \lambda_3 \mathcal{L}_{pl}] \quad (3\text{-}4)$$

where $\lambda_1$ is a weight corresponding to the adversarial loss, $\lambda_2$ is a weight corresponding to the reconstruction loss, and $\lambda_3$ is a weight corresponding to the projection loss. In a schematic example, $\lambda_1 = 0.1$, and $\lambda_2 = \lambda_3 = 10$.

Figure 9:
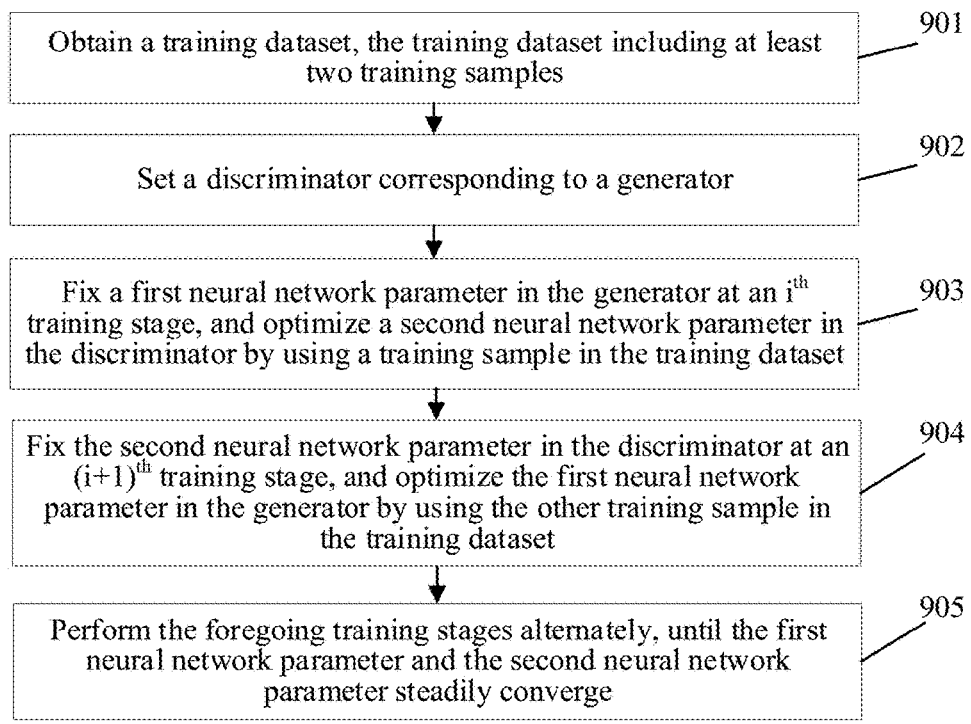
FIG. 9 is a flowchart of a generator training method according to an embodiment of this disclosure.

FIG. 9 is a flowchart of a generator training method according to an embodiment of this disclosure. The training method may be performed by a computer device. The method includes the following steps:

Step 901: Obtain a training dataset, the training dataset including at least two training samples.

The training task of the generator needs a large quantity of pairs of an X-ray film and a CT image to form a training dataset for an X2CT-GAN model to learn a mapping relationship between the X-ray film and the CT images. However, currently, there is no such an open dataset. Therefore, a DRR (Digitally Reconstructured Radiographs) technology is adopted in this embodiment to generate a virtual X-ray film from a real CT image. Schematically, the following steps are included:

firstly, obtain at least two real CT images as sample CT images;

secondly, generate a corresponding first virtual X-ray film and a corresponding second virtual X-ray film for each of the at least two real CT images; where the first virtual X-ray film is an X-ray film from a front viewing angle, and the second virtual X-ray film is an X-ray film from a side viewing angle; and thirdly, designate the at least two real CT images with the corresponding first virtual X-ray films, and the corresponding second virtual X-ray films as the at least two training samples.

The real CT images may be acquired by using different devices from different manufacturers, resulting in severe differences presented in a data size and a resolution. For example, there is a large quantity of slices for some CT images, and there is a relatively small quantity of slices for some CT images. In another example, although resolutions on two coordinate axes in a slice are the same, there is still a difference of the resolution for different CT images. Therefore, in this disclosure, pre-processing is performed to standardize the real CT images. Specifically, there are two steps:

(1) unifying resolutions in all directions of a real CT image through re-sampling as 1×1×1 mm$^3$; and (2) obtaining a cube region with a size of 320×320×320 mm$^3$ from a top part of each real CT image through clipping, an axis with a length less than 320 mm being filled with a zero value.

The real CT images after being processed by the foregoing two steps are endowed with an isotropic feature. Besides, each of the real CT image can cover an entire chest region. If the foregoing processing is performed by using a lung dataset LIDC (The Lung Image Database Consortium)-IDRI (Image Database Resource Initiative) that is already open, the enhanced LIDC-IDRI includes 1018 groups of virtual X-ray films from two viewing angles and a corresponding real CT image thereof. One group of X-ray films from two viewing angles and a corresponding real CT image thereof forms one sample. 916 samples are randomly selected as the training dataset in this embodiment. The remaining 102 samples are used as a test dataset. A ratio of samples in the training dataset to samples in the test dataset is about 9:1.

Step 902: Set a discriminator corresponding to the generator.

The discriminator is constructed based on a PatchDiscriminator under Pix2Pix, which is generalized to a three-dimensional form in this embodiment of this disclosure, and the discriminator is named as 3DPatchDiscriminator. The discriminator is composed of 3 conv3d-norm-relu modules with a convolutional kernel of each being 4 and a stride being 2, 1 conv3d-norm-relu module with a convolutional kernel being 4 and a stride being 1, and one conv3d layer, and outputs a result by using a sigmoid activation function. Specific parameter setting is shown in Table 2.

TABLE 2

| Detailed network setting of discriminator | | |
|---|---|---|
| Layer name | Settings | Output size |
| Conv_0 | [4 × 4 × 4, 64, s = 2], IN, ReLU | 64 × 64 × 64 |
| Conv_1 | [4 × 4 × 4, 128, s = 2], IN, ReLU | 32 × 32 × 32 |
| Conv_2 | [4 × 4 × 4, 256, s = 2], IN, ReLU | 16 × 16 × 16 |
| Conv_3 | [4 × 4 × 4, 512], IN, ReLU | 16 × 16 × 16 |
| Conv_4 | [4 × 4 × 4, 1], Sigmoid | 16 × 16 × 16 |

The training method of the X2CT-GAN is a little different from that of the original GAN, but the overall training concept is still that the generator and the discriminator are trained alternately. The training is performed based on an enhanced LIDC-IDRI dataset. During the training, parameters of the network are updated by using an optimization algorithm based on a gradient loss, to enable (x, y) to represent a sample including a pair of X-ray films from two viewing angles and a CT dataset. The optimization algorithm based on a gradient loss includes any one of an Adam optimization algorithm, an SGD optimization algorithm, and an RMSProp optimization algorithm.

Step 903: Fix a first neural network parameter in the generator at an $i^{th}$ training stage, and optimize a second neural network parameter in the discriminator by using a training sample in the training dataset.

A gradient of the discriminator is calculated by using the following formula (3-5). Then the second neural network parameter in the discriminator is updated by using the optimization algorithm based on a gradient loss.

$$\nabla_{\theta_d} \frac{1}{2m} \sum_{i=1}^{m} [(D(y|x) - 1)^2 + (D(G(x)|x) - 0)^2] \quad (3-5)$$

where m is a total quantity of the training samples, and Od is the second neural network parameter in the discriminator.

Step 904: Fix the second neural network parameter in the discriminator at an $(i+1)^{th}$ training stage, and optimize the first neural network parameter in the generator by using the other training sample in the training dataset.

The calculation of a gradient of the generator is relatively complex. At first, the adversarial loss of the generator is calculated according to the formula (3-6), the reconstruction loss is calculated according to the formula (3-7), and the projection loss is calculated according to the formula (3-8); next, the gradient is calculated according to the formula (3-9) ($\lambda_1$=0.1, $\lambda_2$=$\lambda_3$=10 in the formula); and then the first neural network parameter in the generator is updated by using the optimization algorithm based on a gradient loss.

$$\mathcal{L}_{LSGAN}(G) = \frac{1}{2m} \sum_{i=1}^{m} [(D(G(x)|x) - 1)^2] \quad (3-6)$$

$$\mathcal{L}_{re} = \frac{1}{m} \sum_{i=1}^{m} [\|y - G(x)\|_2^2] \quad (3-7)$$

$$\mathcal{L}_{pl} = \frac{1}{3m} \sum_{i=1}^{m} [\|P_{ax}(y) - P_{ax}(G(x))\|_1 + \quad (3-8)$$
$$\|P_{co}(y) - P_{co}(G(x))\|_1 + \|P_{sa}(y) - P_{sa}(G(x))\|_1]$$

$$\nabla_{\theta_g}[\lambda_1 \mathcal{L}_{LSGAN}(G) + \lambda_2 \mathcal{L}_{re} + \lambda_3 \mathcal{L}_{pl}] \quad (3-9)$$

where m is a total quantity of the training samples, and $\theta_g$ is the first neural network parameter in the generator.

Step 905: Perform the foregoing training stages alternately, until the first neural network parameter and the second neural network parameter steadily converge.

An example in which the parameters of the network is optimized by using an Adam optimizer is used. An initial learning rate $Lr_{init}$=2e-4, and momentum parameters $\beta_1$=0.5 and $\beta_2$=0.99. In the first 50 iteration cycles, such a group of parameters keep unchanged. After then a policy that a learning rate is linearly attenuated is adopted. Compared with the setting of a constant learning rate, such a manner is beneficial for the network to converge to a better position. A specific operation is to attenuate the learning rate to 0 according to the formula (3-10), where Lr_iter represents a learning rate in a current iteration cycle, iter represents a current quantity of times of iteration, and max_iter represents a total quantity of times of iteration, which is set to 100 in an experiment.

$$Lr_{iter} = \left(1 - \frac{iter - 50}{\max\_iter - 50}\right) \times Lr_{init} \quad (3-10)$$

Figure 10:
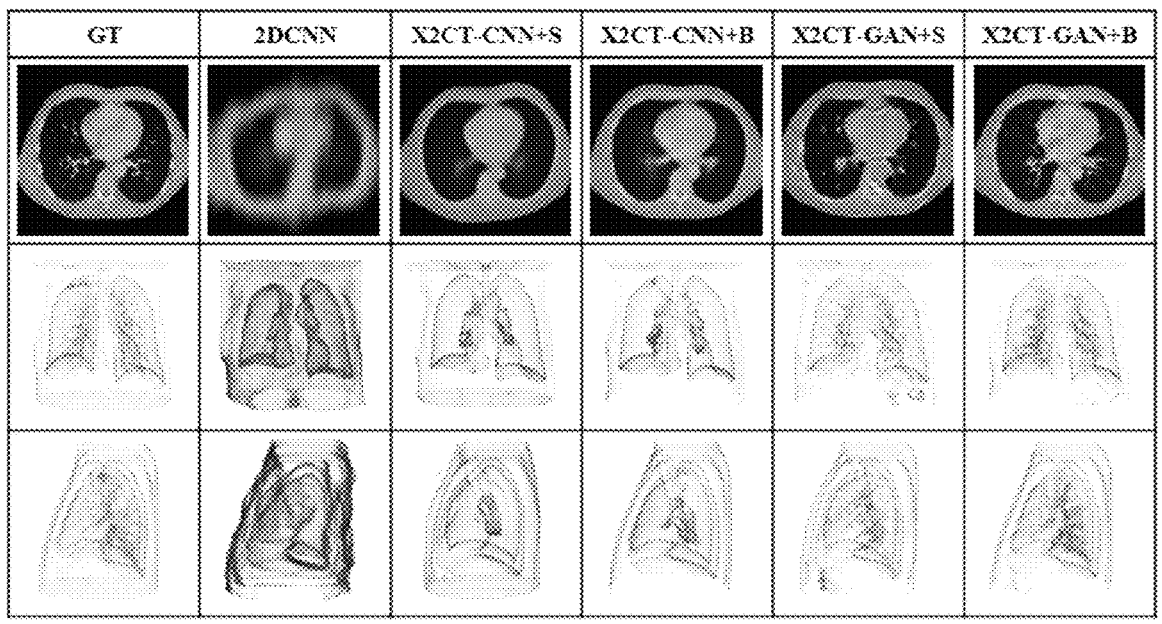
FIG. 10 is an effect comparison diagram of reconstructing a CT image by using different neural network models according to an embodiment of this disclosure.

FIG. 10 shows comparison between reconstruction results of reconstruction of a CT image by using different neural network models during an experiment. At first, model types for comparison in the first row in FIG. 10 are simply illustrated. "GT", that is, ground truth, represents a benchmark for reconstruction, that is, a CT image used as a reference criterion (such as, a real CT image); "2DCNN" represents a model that a CT image is reconstructed by using a two-dimensional convolutional neural network; "X2CT-CNN+S" represents a model that a CT image is reconstructed by using one X-ray film as a single-view input, and using a three-dimensional convolutional neural network, and correspondingly, "X2CT-CNN+B" represents a model that a CT image is reconstructed by using two orthogonal X-ray films as a two-view input, and using a three-dimensional convolutional neural network; and "X2CT-GAN" is a model based on a GAN supervisory signal provided in the foregoing embodiments. The first column of the second row in FIG. 10 displays a slice of a CT image of a patient that is selected from a test set. The remaining columns of the second row display reconstruction results of the neural network models. The third row and the fourth row in FIG. 10 respectively show three-dimensional visualization results of the sample data from a front viewing angle and a side viewing angle, to help a reader to more intuitively compare differences between reconstruction results of different neural network models in a three-dimensional space.

Because the 2DCNN model can only process a case of a single-view input, no result of a two-view input of the 2DCNN model is given herein. It can be seen obviously from FIG. 10 that a result outputted by the 2DCNN model is rather obscure and the shape is severely deformed. In comparison, the X2CT-CNN model can capture a clear edge, which fully indicates that a model combining both two-dimensional convolution and three-dimensional convolution is far better than a purely two-dimensional convolutional network in a fitting capability. Besides, to test an advantage of the two-view input relative to the single-view input, it can be seen from side-direction three-dimensional visualization results in FIG. 10 that, because there is no input information in such a direction for the model with a single-view input, there is a relatively large discrepancy between reconstruction results while the model with a two-view input can well impose a correct limit during the reconstruction, so as to produce a more accurate reconstruction result.

Besides, an improvement effect on details by the X2CT-GAN can be further observed intuitively from FIG. 10. The X2CT-CNN with a two-view input uses only a voxel-level reconstruction loss for network optimization. Therefore, the result obtained is quite good in terms of a general shape and contour, but the edges are extremely smooth and lack a lot of details, which is very easy for human eyes to distinguish real data and reconstructed data. The X2CT-GAN model based on a GAN gives full play to the capability of the GAN to learn real data distribution. The reconstruction results can capture fine structures such as blood vessels in lungs and visually are closer to real CT images. For ordinary people who lack professional medical knowledge training, it is difficult to distinguish the reconstructed data generated by the model from the real data in a short time. The X2CT-GAN model with a two-view input already can relatively accurately reconstruct main organs (such as lungs or a heart), and therefore has a certain clinical value, such as organ size measurement, a thoracic deformity diagnosis, and radiotherapy dose planning.

Figure 11:
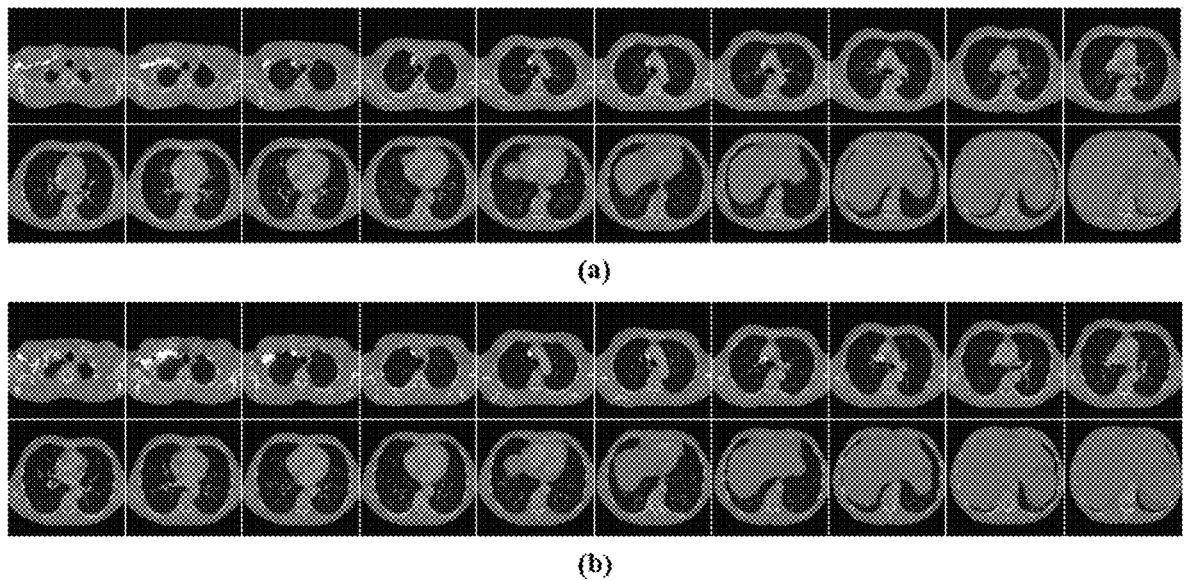
FIG. 11 is a schematic comparison diagram of comparing a reconstructed CT image and a real CT image of a single illness case slice by slice according to an embodiment of this disclosure.

Using a single case as an example, FIG. 11 is a schematic diagram of comparing reconstructed CT images reconstructed by the generator and real CT images one by one according to an embodiment of this disclosure.

Figure 12:
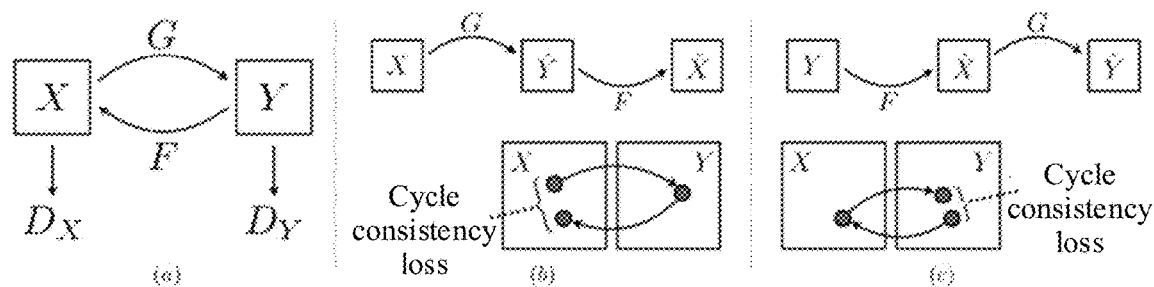
FIG. 12 is a schematic diagram of mapping between real X-ray films and virtual X-ray films according to an embodiment of this disclosure.

To evaluate the accuracy of reconstructing complete CT data from real X-ray films, the indispensable link is to test the model provided in the embodiments of this disclosure by using the real X-ray films. Although the X2CT-GAN model is trained by using virtual data, with the aid of the CycleGAN model, this disclosure achieves a leap from a real X-ray film to a virtual X-ray film. In an example, 200 real X-ray films and 200 virtual X-ray films are collected, and the CycleGAN model learns mutual conversion between the two, as shown in FIG. 12. X represents image domain formed by the 200 real X-ray films, and Y represents image domain formed by the 200 virtual X-ray films. It is assumed that mapping from the domain X to the domain Y that needs to be learned is set to G (generator), and reverse mapping is set to F (generator). There is a discriminator $D_Y$ in the domain Y, and there is a discriminator $D_X$ in the domain X. Training in a manner of adversarial learning not only requires the discriminator to distinguish between real X-ray films and virtual X-ray films as much as possible, but also requires an error after two times of mapping to be as small as possible, that is, $F(G(X))\approx X$, and $G(F(Y))\approx Y$. The error may be expressed by using a cycle consistency loss. $\hat{X}$ represents a mapped X, and $\hat{Y}$ represents a mapped Y.

Figure 13:
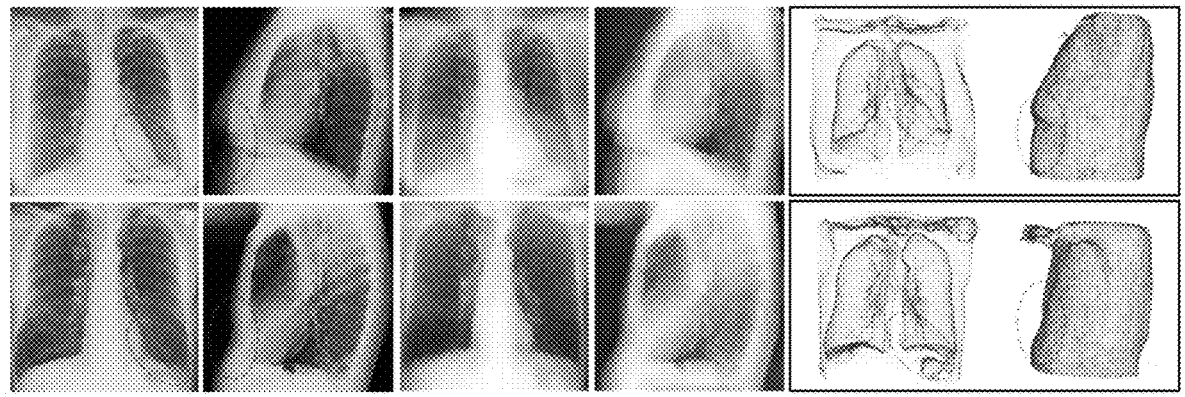
FIG. 13 is a diagram of a conversion principle of a CycleGAN model according to an embodiment of this disclosure.

After the CycleGAN model steadily converges, and before the X2CT-GAN model is tested by using the real X-ray films, the real X-ray films is converted into a style of virtual X-ray films by using merely a generator from real X-ray films to virtual X-ray films in the CycleGAN, and then the converted X-ray films are used for CT reconstruction test. A test result is shown as FIG. 13. The first two columns are two real X-ray films from different viewing angles, the next two columns are X-ray films converted by using the CycleGAN, and the last two columns display three-dimensional visualization results of an internal structure and a surface structure of a reconstructed CT. A dashed ellipse marks a high-quality reconstruction region. It can be seen from the reconstruction results that reconstruction of a real X-ray film by using the X2CT-GAN model provided in this embodiment is also very proper, especially for a lung region and a surface contour. An obvious line-bending change may be seen in a region circled by the dashed ellipse in the real X-ray film shown in FIG. 13. Such a change can be accurately captured by the model and can be embodied in the reconstruction result.

Application Scenario of Generator

Figure 14:
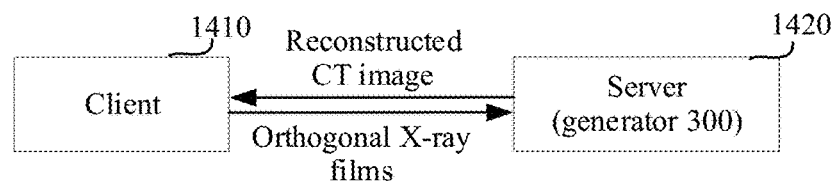
FIG. 14 is a diagram of an application scenario of a generator according to an embodiment of this disclosure.

In an embodiment shown in FIG. 14, the foregoing generator 300 may be deployed in a server 1420. After a client 1410 transmits two orthogonal X-ray films to the server 1420, the server 1420 calls the generator 300 to generate a reconstructed CT image, and the server 1420 transmits the reconstructed CT image to the client 1410.

Figure 15:
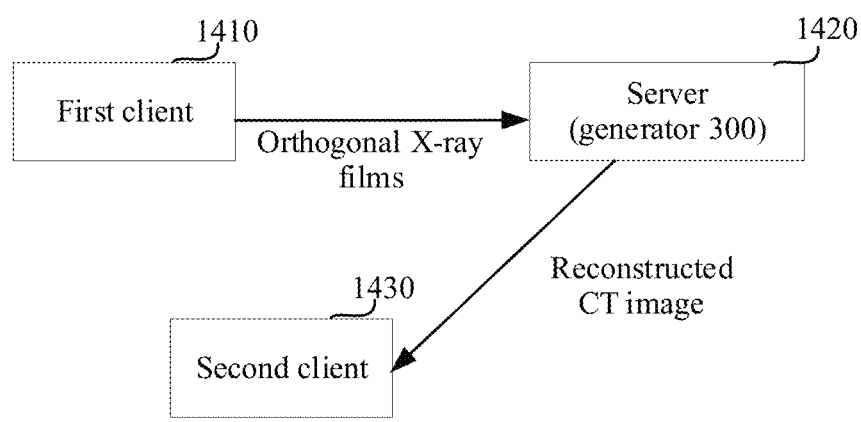
FIG. 15 is a diagram of an application scenario of a generator according to an embodiment of this disclosure.

In another embodiment shown in FIG. 15, the foregoing generator 300 may be deployed in a server 1420. After a first client 1410 transmits two orthogonal X-ray films to the server 1420, the server 1420 calls the generator 300 to generate a reconstructed CT image, and the server 1420 transmits the reconstructed CT image to a second client 1430.

Figure 16:
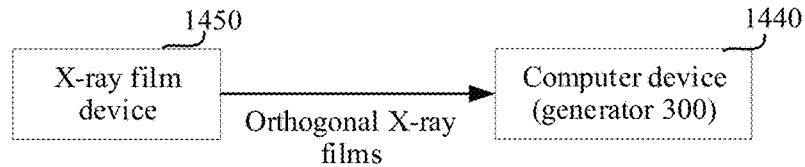
FIG. 16 is a diagram of an application scenario of a generator according to an embodiment of this disclosure.

In another embodiment shown in FIG. 16, the foregoing generator 300 may be deployed in a computer device 1440 connected to an X-ray film device 1450. After the X-ray film device transmits two orthogonal X-ray films to the computer device 1440, the computer device 1440 calls the generator 300 to generate a reconstructed CT image, and the computer device 1440 displays the reconstructed CT image to a doctor or a patient for a check.

Figure 17:
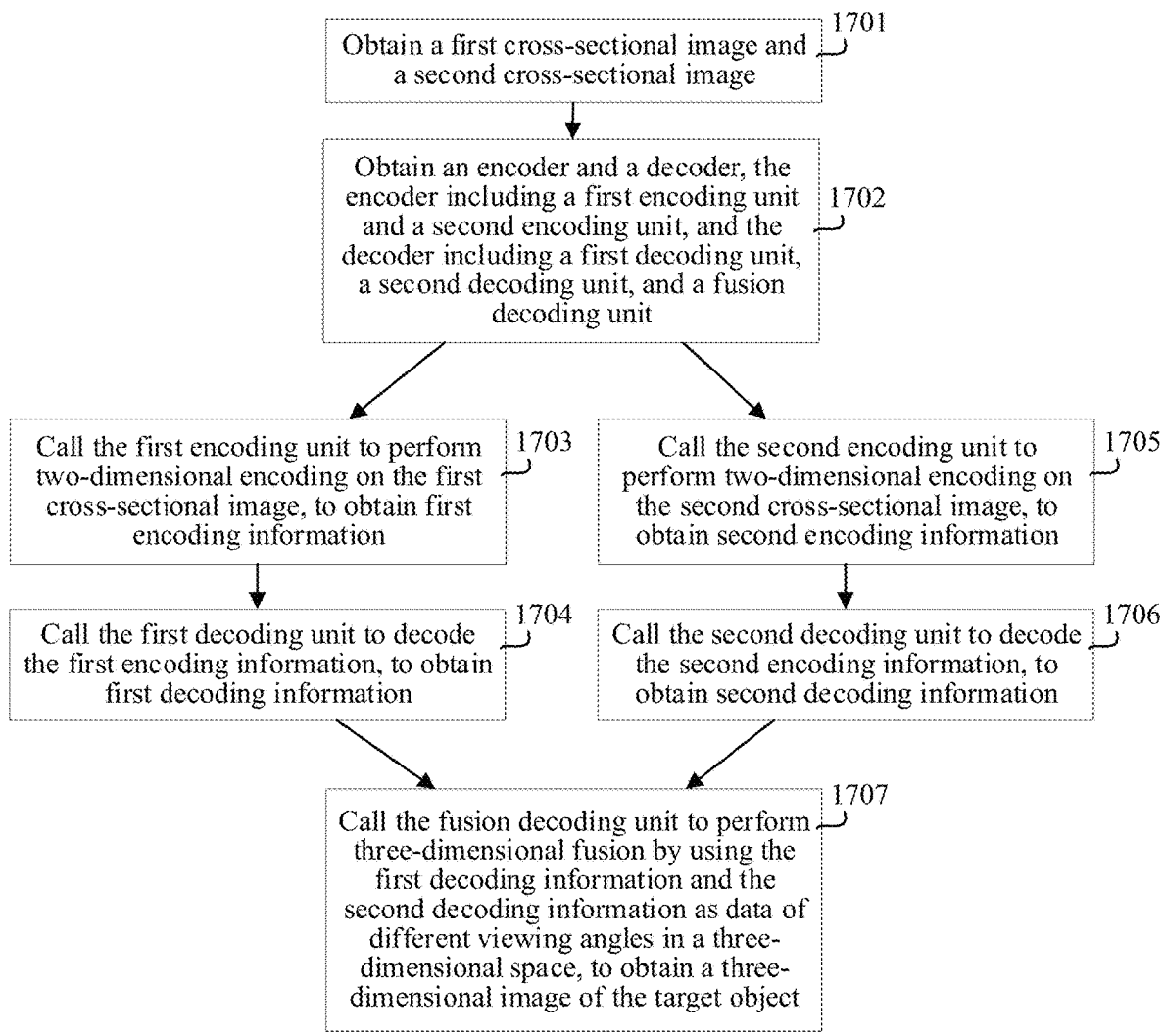
FIG. 17 is a flowchart of a three-dimensional image synthetic method according to an embodiment of this disclosure.

FIG. 17 is a flowchart of a three-dimensional image synthetic method according to an embodiment of this disclosure. The method may be implemented by a computer device. The method includes the following steps:

Step 1701: Obtain a first cross-sectional image and a second cross-sectional image, the first cross-sectional image and the second cross-sectional image being images acquired for a target object from two orthogonal viewing angles.

Exemplarily, the first cross-sectional image is an image acquired for the target object from a first viewing angle, and the second cross-sectional image is an image acquired for the target object from a second viewing angle. The first viewing angle and the second viewing angle are two mutually orthogonal viewing angles.

Step 1702: Obtain an encoder and a decoder, the encoder including a first encoding unit and a second encoding unit, and the decoder including a first decoding unit, a second decoding unit, and a fusion decoding unit.

Exemplarily, the encoder and the decoder are implemented by using the neural network architectures shown in FIG. 3 and FIG. 4. The encoder and the decoder are constructed by using a GAN.

In this embodiment, network structures of the encoder and the decoder are not repeated.

Step 1703: Call the first encoding unit to perform two-dimensional encoding on the first cross-sectional image, to obtain first encoding information.

Step 1704: Call the first decoding unit to decode the first encoding information, to obtain first decoding information.

Step 1705: Call the second encoding unit to perform two-dimensional encoding on the second cross-sectional image, to obtain second encoding information.

Step 1706: Call the second decoding unit to decode the second encoding information, to obtain second decoding information.

Step 1707: Call the fusion decoding unit to perform three-dimensional fusion by using the first decoding information and the second decoding information as data of different viewing angles in a three-dimensional space, to obtain a three-dimensional image of the target object.

Based on the above, in the method provided in this embodiment, two orthogonal cross-sectional images are separately inputted into an encoder for encoding, and then encoding information are decoded through two decoding units in a decoder. Fusion decoding is performed on two types of decoding information by a fusion decoding unit in the decoder, to obtain a three-dimensional image of a target object through fusion, so that an effect of the three-dimensional image of the target object may be restored only by obtaining two cross-sectional images. Therefore, the three-dimensional image of the target object can be obtained without a three-dimensional scanner.

It is to be understood that although the steps in the flowcharts of FIG. 1, FIG. 9, and FIG. 17 are sequentially displayed in accordance with instructions indicated by arrows, these steps are not necessarily performed sequentially in the order indicated by the arrows. Unless otherwise explicitly specified in this disclosure, execution of the steps is not strictly limited, and the steps may be performed in other sequences. Moreover, at least some of the steps in FIG. 1, FIG. 9, and FIG. 17 may include a plurality of sub-steps or a plurality of stages. These sub-steps or stages are not necessarily performed at the same moment, but may be performed at different times. These sub-steps or stages are not necessarily executed sequentially, but may be performed with at least one part of the other steps or sub-steps of other steps or stages in turn.

Figure 18:
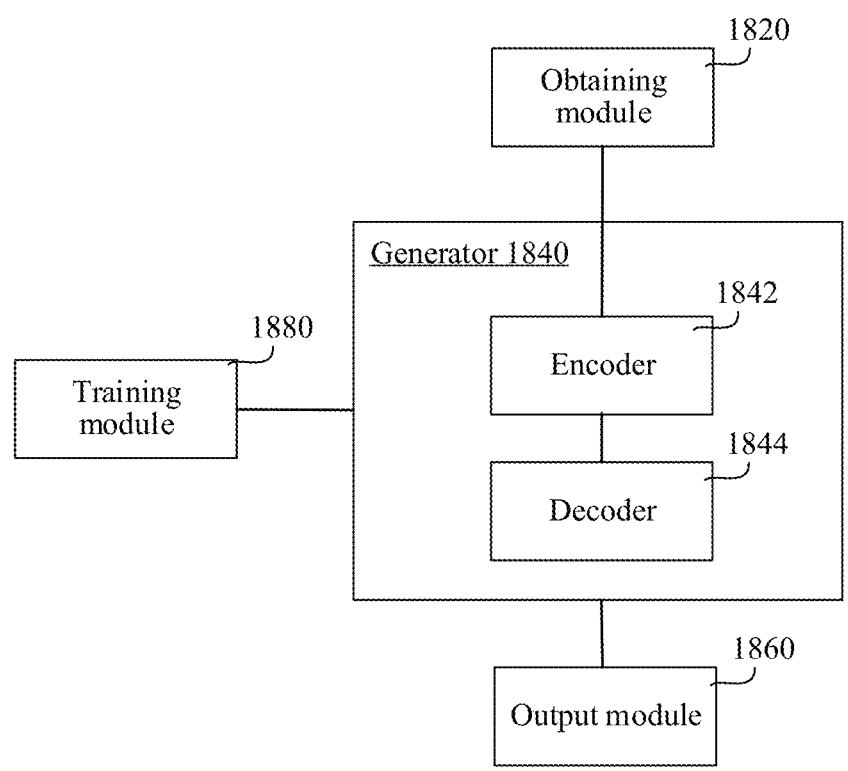
FIG. 18 is a block diagram of a CT image generation apparatus according to an embodiment of this disclosure.

FIG. 18 is a block diagram of a CT image generation apparatus according to an embodiment of this disclosure. The apparatus may be implemented as an entire computer device or a part of the computer device by using software, hardware, or a combination thereof. The apparatus includes: an obtaining module 1820, a generation module 1840, and an output module 1860.

The obtaining module 1820 is configured to obtain a first X-ray film and a second X-ray film, the first X-ray film and the second X-ray film being X-ray films acquired for a target object from two orthogonal viewing angles.

The generation module 1840 is configured to perform three-dimensional reconstruction on the first X-ray film and the second X-ray film, to obtain a three-dimensional model of the target object.

The output module 1860 is configured to obtain a CT image of the target object according to the three-dimensional model of the target object.

In an embodiment, the generation module 1840 includes an encoder 1842 and a decoder 1844.

The encoder 1842 is configured to separately encode the first X-ray film and the second X-ray film, to obtain first encoding information and second encoding information; and the decoder 1844 is configured to perform three-dimensional reconstruction decoding on the first encoding information and the second encoding information, to obtain the three-dimensional model of the target object.

In an embodiment, the encoder 1842 includes a first encoding unit and a second encoding unit; and the decoder 1844 includes a first decoding unit, a second decoding unit, and a fusion decoding unit.

The first encoding unit is configured to perform two-dimensional encoding on the first X-ray film, to obtain the first encoding information;

the second encoding unit is configured to perform two-dimensional encoding on the second X-ray film, to obtain the second encoding information;

the first decoding unit is configured to decode the first encoding information, to obtain first decoding information;

the second decoding unit is configured to decode the second encoding information, to obtain second decoding information; and the fusion decoding unit is configured to perform three-dimensional fusion by using the first decoding information and the second decoding information as data of different viewing angles in a three-dimensional space, to obtain the three-dimensional model of the target object.

In an embodiment, at least one encoding unit of the first encoding unit and the second encoding unit includes n+2 encoding layers, the n+2 encoding layers including:

a two-dimensional convolutional layer, n cascaded densely-connected layer, and a pooling layer, the two-dimensional convolutional layer being connected to the first densely-connected layer, the $n^{th}$ densely-connected layer being connected to the pooling layer, n being a positive integer.

In an embodiment, the first encoding unit is connected to the first decoding unit through a connection-A, and/or the second encoding unit is connected to the second decoding unit through the connection-A.

The connection-A is used for converting encoding information in a two-dimensional form into encoding information in a three-dimensional form.

In an embodiment, the connection-A is used for expanding the encoding information in a two-dimensional form into a first one-dimensional vector, stretching the first one-dimensional vector into a second one-dimensional vector, and rearranging the second one-dimensional vector into the encoding information in a three-dimensional form.

In an embodiment, at least one decoding unit of the first decoding unit and the second decoding unit includes n+2 decoding layers, the n+2 decoding layers including: an up-sampling layer, n cascaded up-convolutional layers, and a three-dimensional convolutional layer, the up-sampling layer being connected to the first up-convolutional layer, the $n^{th}$ up-convolutional layer being connected to the three-dimensional convolutional layer, n being a positive integer.

In an embodiment, the decoding unit 1844 further includes n connections-C, a first input terminal of an $i^{th}$ connection-C being connected to an output terminal of an $i^{th}$ decoding layer in the decoding unit, a second input terminal of the $i^{th}$ connection-C being connected to an output terminal of an $(i+1)^{th}$ encoding layer in a corresponding encoding unit, and an output terminal of the $i^{th}$ connection-C being connected to an input terminal of an $(i+1)^{th}$ decoding layer in the decoding unit.

The connection-C is used for performing weighted summation on three-dimensional decoding information inputted from the first input terminal and three-dimensional encoding information inputted from the second input terminal, and using an outputted result as an input of a next decoding layer.

In an embodiment, the connection-C is used for performing, after transforming the three-dimensional decoding information inputted from the first input terminal and the three-dimensional encoding information inputted from the second input terminal into the same three-dimensional space, weighted summation on the three-dimensional decoding information and the three-dimensional encoding information in the three-dimensional space, and using an outputted result as the input of the next decoding layer.

In an embodiment, the second input terminal of the $i^{th}$ connection-C is further connected to an output terminal of an $(i+1)^{th}$ encoding layer in the corresponding encoding unit through an $i^{th}$ connection-B.

The $i^{th}$ connection-B is used for converting two-dimensional encoding information outputted by the $(i+1)^{th}$ encoding layer into three-dimensional encoding information.

In an embodiment, the $i^{th}$ connection-B is used for expanding the two-dimensional encoding information outputted by the $(i+1)^{th}$ encoding layer into m layers in a vertical dimension, and determining expanded two-dimensional encoding information of m layers as the three-dimensional encoding information, m being a positive integer.

In an embodiment, the fusion decoding unit includes n+2 fusion decoding layers, the n+2 fusion decoding layers including:

an up-sampling layer, n cascaded up-convolutional layers, and a three-dimensional convolutional layer, an output terminal of the up-sampling layer being connected to the first up-convolutional layer, and the $n^{th}$ up-convolutional layer being connected to the three-dimensional convolutional layer.

In an embodiment, the fusion decoding unit further includes a connection-C, a first input terminal of the connection-C being connected to an input terminal of the first decoding unit, a second input terminal of the connection-C being connected to an input terminal of the second decoding unit, and an output terminal of the connection-C being connected to an input terminal of the up-sampling layer.

The connection-C is used for performing weighted summation on three-dimensional encoding information inputted from the first input terminal and three-dimensional encoding information inputted from the second input terminal, and using an outputted result as an input of a next fusion decoding layer.

In an embodiment, the fusion decoding unit further includes n compound connections-C, each of the compound connections-C including a first connection-C and a second connection-C.

A first input terminal of an $i^{th}$ first connection-C is connected to an output terminal of an $(i+1)^{th}$ decoding layer in the first decoding unit, a second input terminal of the $i^{th}$ first connection-C is connected to an output terminal of an $(i+1)^{th}$ decoding layer in the second decoding unit, an output terminal of the $i^{th}$ first connection-C is connected to a first input terminal of an it second connection-C, a second input terminal of the it second connection-C is connected to an output terminal of an $i^{th}$ fusion decoding layer in the fusion decoding unit, and an output terminal of the $i^{th}$ second connection-C is connected to an input terminal of an $(i+1)^{th}$ fusion decoding layer in the fusion decoding unit.

In an embodiment, the generator is trained based on a GAN, a loss function of the generator including:

an adversarial loss; or the adversarial loss and a reconstruction loss; or the adversarial loss and a projection loss; or the adversarial loss, the reconstruction loss, and the projection loss, where the adversarial loss is used for representing a semantic loss between the three-dimensional model reconstructed by the generator and a sample CT image, the reconstruction loss is used for representing a pixel-level discrepancy loss between the three-dimensional model reconstructed by the generator and the sample CT image, and the projection loss is used for representing a discrepancy loss between the three-dimensional model reconstructed by the generator and the sample CT image on at least one projection plane.

In an embodiment, the apparatus further includes a training module 1880.

The training module 1880 is configured to obtain a training dataset, the training dataset including at least two training samples; set a discriminator corresponding to the generator; fix a first neural network parameter in the generator at an $i^{th}$ training stage, and optimize a second neural network parameter in the discriminator by using a training sample in the training dataset; fix the second neural network parameter in the discriminator at an $(i+1)^{th}$ training stage, and optimize the first neural network parameter in the generator by using the other training sample in the training dataset; and perform the foregoing two training stages alternately, until the first neural network parameter and the second neural network parameter steadily converge.

In an embodiment, the training module 1880 is configured to obtain at least two real CT images as the sample CT image; generate a corresponding first virtual X-ray film and a corresponding second virtual X-ray film for each of the at least two real CT images; and determine first virtual X-ray films, second virtual X-ray films, and the real CT images that correspond to each other as the at least two training samples.

Figure 19:
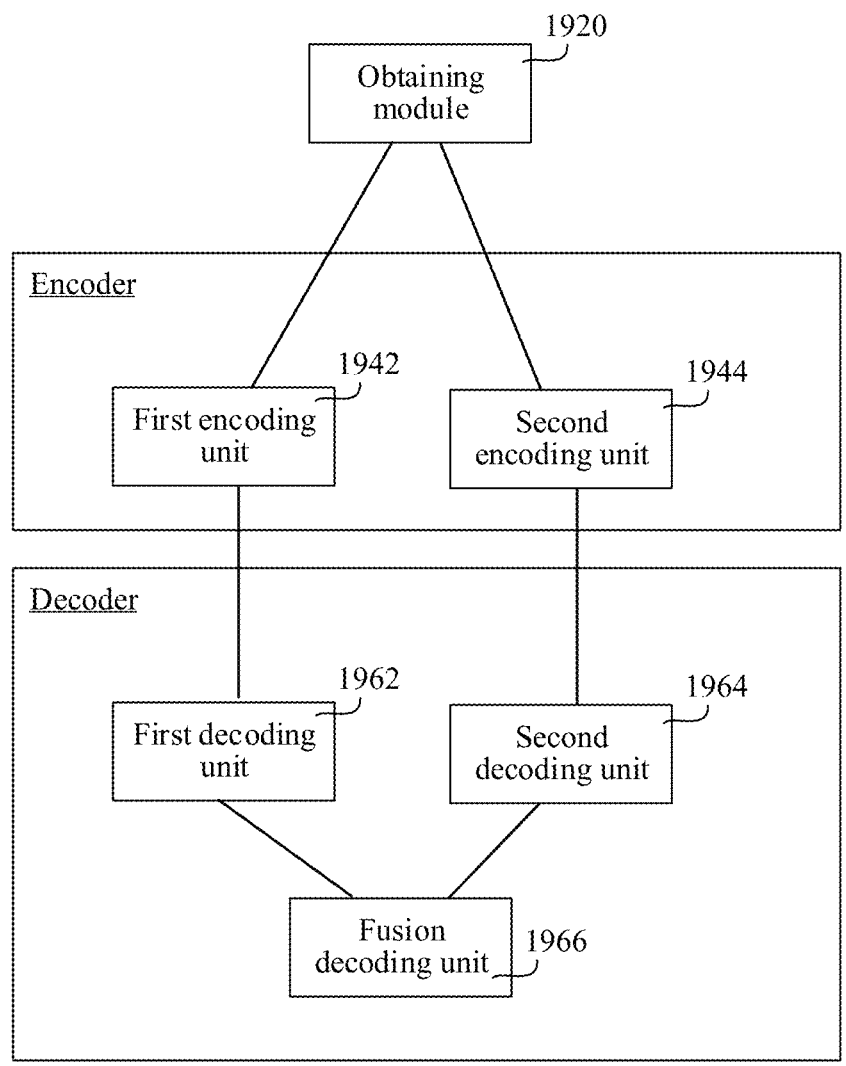
FIG. 19 is a block diagram of a three-dimensional image synthetic apparatus according to an embodiment of this disclosure.

FIG. 19 is a block diagram of a three-dimensional image synthetic apparatus according to an embodiment of this disclosure. The apparatus may be implemented as an entire computer device or a part of the computer device by using software, hardware, or a combination thereof. The apparatus includes an obtaining module 1920, a first encoding unit 1942, a second encoding unit 1944, a first decoding unit 1962, a second decoding unit 1964, and a fusion decoding unit 1966.

The obtaining module 1920 is configured to obtain a first cross-sectional image and a second cross-sectional image, the first cross-sectional image and the second cross-sectional image being images obtained after a target object is sectioned by using two orthogonal cross sections.

The obtaining module 1920 is further configured to obtain an encoder and a decoder. The encoder includes the first encoding unit 1942 and the second encoding unit 1944, and the decoder includes the first decoding unit 1962, the second decoding unit 1964, and the fusion decoding unit 1966.

The first encoding unit 1942 is configured to perform two-dimensional encoding on the first cross-sectional image, to obtain first encoding information.

The first decoding unit 1962 is configured to decode the first encoding information, to obtain first decoding information.

The second encoding unit 1944 is configured to perform two-dimensional encoding on the second cross-sectional image, to obtain second encoding information.

The second decoding unit 1964 is configured to decode the second encoding information, to obtain second decoding information.

The fusion decoding unit 1966 is configured to perform three-dimensional fusion by using the first decoding information and the second decoding information as data of different viewing angles in a three-dimensional space, to obtain a three-dimensional image of the target object.

Based on the above, through the apparatus provided in this embodiment, two orthogonal cross-sectional images are separately inputted into an encoder for encoding, and then encoding information are decoded through two decoding units in a decoder. Fusion decoding is performed on two types of decoding information by a fusion decoding unit in the decoder, to obtain a three-dimensional image of a target object through fusion, so that an effect of the three-dimensional image of the target object may be restored only by obtaining two cross-sectional images. Therefore, the three-dimensional image of the target object can be obtained without a three-dimensional scanner.

Figure 20:
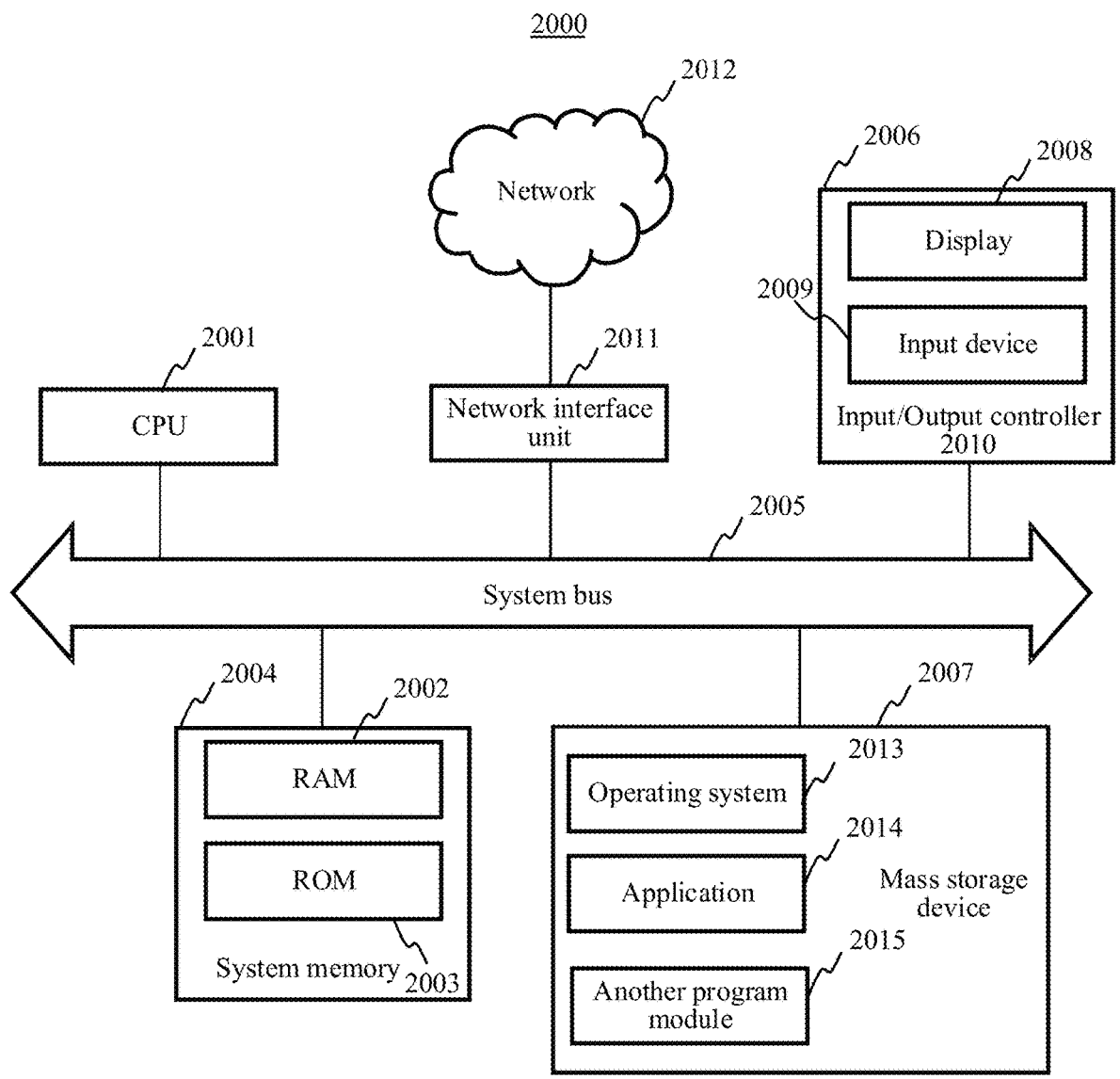
FIG. 20 is a block diagram of a computer device according to an embodiment of this disclosure.

FIG. 20 is a schematic structural diagram of a computer device according to an embodiment of this disclosure. Schematically, a computer device 2000 includes a central processing unit (CPU) 2001, a system memory 2004 including a random access memory (RAM) 2002 and a read-only memory (ROM) 2003, and a system bus 2005 connecting the system memory 2004 and the CPU 2001. The computer device 2000 further includes a basic input/output system (I/O system) 2006 configured to transmit information between components in a computer, and a mass storage device 2007 configured to store an operating system 2013, a client 2014, and another program module 2015.

The basic I/O system 2006 includes a display 2008 configured to display information and an input device 2009 such as a mouse or a keyboard that is configured to input information by a user. The display 2008 and the input device 2009 are both connected to the CPU 2001 by using an input/output controller 2010 connected to the system bus 2005. The basic I/O system 2006 may further include the input/output controller 2010, to receive and process inputs from a plurality of other devices, such as the keyboard, the mouse, or an electronic stylus. Similarly, the input/output controller 2010 further provides an output to a display screen, a printer, or another type of output device.

The mass storage device 2007 is connected to the CPU 2001 by using a mass storage controller (not shown) connected to the system bus 2005. The mass storage device 2007 and an associated computer-readable medium provide non-volatile storage for the computer device 2000. That is, the mass storage device 2007 may include a computer-readable medium (not shown) such as a hard disk or a compact disc ROM (CD-ROM) drive.

Without loss of generality, the computer-readable medium may include a computer storage medium and a communication medium. The computer storage medium includes volatile and non-volatile media, and removable and non-removable media implemented by using any method or technology used for storing information such as computer-readable instructions, data structures, program modules, or other data. The computer storage medium includes a RAM, a ROM, an erasable programmable ROM (EPROM), an electrically erasable programmable ROM (EEPROM), a flash memory or another solid-state memory technology, a CD-ROM, a digital versatile disc (DVD) or another optical memory, a tape cartridge, a magnetic cassette, a magnetic disk memory, or another magnetic storage device. Certainly, it may be known by a person skilled in the art that the computer storage medium is not limited to the foregoing several types. The system memory 2004 and the mass storage device 2007 may be collectively referred to as a memory.

According to the various embodiments of this disclosure, the computer device 2000 may further be connected, through a network such as the Internet, to a remote computer on the network for running. That is, the computer device 2000 may be connected to a network 2012 by using a network interface unit 2011 connected to the system bus 2005, or may be connected to another type of network or a remote computer system (not shown) by using a network interface unit 2011.

This disclosure further provides a computer-readable storage medium, the computer-readable storage medium storing at least one instruction, at least one program, a code set or an instruction set, the at least one instruction, the at least one program, the code set or the instruction set being loaded and executed by the processor to implement the CT image generation method or the three-dimensional image synthetic method provided in the foregoing method embodiments.

Exemplarily, this disclosure further provides a computer program product including instructions, the instructions causing, when run on a computer device, the computer device to perform the CT image generation method or the three-dimensional image synthetic method provided in the foregoing method embodiments.

A person of ordinary skill in the art may understand that all or some of the steps of the foregoing embodiments may be implemented by hardware, or may be implemented by a program instructing relevant hardware. The program may be stored in a computer-readable storage medium. The storage medium may be a ROM, a magnetic disk, an optical disc, or the like.

The term module (and other similar terms such as unit, submodule, subunit, etc.) in this disclosure may refer to a software module, a hardware module, or a combination thereof. A software module (e.g., computer program) may be developed using a computer programming language. A hardware module may be implemented using processing circuitry and/or memory. Each module can be implemented using one or more processors (or processors and memory). Likewise, a processor (or processors and memory) can be used to implement one or more modules. Moreover, each module can be part of an overall module that includes the functionalities of the module.

The foregoing descriptions are merely preferred embodiments of this disclosure, and are not intended to limit this disclosure. Any modification, equivalent replacement, improvement, and the like made within the spirit and principle of this disclosure shall fall within the protection scope of this disclosure.

What is claimed is:

1. A Computed Tomography (CT) image generation method, performed by a computer device, the method comprising:

obtaining a first X-ray image and a second X-ray image, the first X-ray image and the second X-ray image being X-ray images acquired for a target object from two orthogonal viewing angles;

performing, by using a generator, three-dimensional reconstruction based on the first X-ray image and the second X-ray image to obtain a three-dimensional model of the target object, the generator comprising an encoder and a decoder, the encode including a first encoding unit and a second encoding unit and the decoder including a first decoding unit, a second decoding unit, and a fusion decoding unit, wherein performing three-dimensional reconstruction comprises:

decoding, by using the first decoding unit, first encoding information from the first encoding unit to obtain first decoding information;

decoding, by using the second decoding unit, second encoding information from the second encoding unit, to obtain second decoding information; and performing, via the fusion decoding unit, three-dimensional fusion by using the first decoding information and the second decoding information as data of different viewing angles in a three-dimensional space to obtain the three-dimensional model of the target object; and obtaining a CT image of the target object according to the three-dimensional model of the target object.

2. The method according to claim 1, wherein:

the generator comprises an encoder and a decoder; and performing, by using the generator, the three-dimensional reconstruction based on the first X-ray image and the second X-ray image to obtain the three-dimensional model of the target object comprises:

separately encoding, by using the encoder, the first X-ray image and the second X-ray image to obtain the first encoding information and the second encoding information; and performing, by using the decoder, three-dimensional reconstruction decoding on the first encoding information and the second encoding information to obtain the three-dimensional model of the target object.

3. The method according to claim 2, wherein:

separately encoding, by using the encoder, the first X-ray image and the second X-ray image to obtain the first encoding information and the second encoding information comprises:

performing, by using the first encoding unit, two-dimensional encoding on the first X-ray image to obtain the first encoding information; and performing, by using the second encoding unit, two-dimensional encoding on the second X-ray image to obtain the second encoding information.

4. The method according to claim 3, further comprising:

providing output of the first encoding unit to the first decoding unit through a connection-A, the connection-A being used for converting the first encoding information in a two-dimensional form into encoding information in a three-dimensional form.

5. The method according to claim 4, wherein performing, by using the generator, three-dimensional reconstruction based on the first X-ray image and the second X-ray image to obtain the three-dimensional model of the target object comprises:

expanding, by using the connection-A, the first encoding information in a two-dimensional form into a first one-dimensional vector;

stretching the first one-dimensional vector into a second one-dimensional vector; and rearranging the second one-dimensional vector into the encoding information in the three-dimensional form.

6. The method according to claim 3, wherein the first decoding unit comprises a neural network of n+2 decoding layers, the n+2 decoding layers comprising:

an up-sampling layer, n cascaded up-convolutional layers, and a three-dimensional convolutional layer, the up-sampling layer being connected to the first up-convolutional layer, the $n^{th}$ up-convolutional layer being connected to the three-dimensional convolutional layer, n being a positive integer, wherein the first decoding unit further comprises n connections-C, a first input terminal of an $i^{th}$ connection-C of the n connections-C being connected to an output terminal of an $i^{th}$ decoding layer of the n+2 decoding layers in the first decoding unit, a second input terminal of the $i^{th}$ connection-C being connected to an output terminal of an $(i+1)^{th}$ encoding layer in the first encoding unit, and an output terminal of the $i^{th}$ connection-C of the n connections-C being connected to an input terminal of an $(i+1)^{th}$ decoding layer of the n+2 decoding layers in the first decoding unit, wherein the $i^{th}$ connection-C is used for performing weighted summation on three-dimensional decoding information inputted from the first input terminal and three-dimensional encoding information inputted from the second input terminal, and providing a result of the weighted summation as an input of the $(i+1)^{th}$ decoding layer, wherein decoding, by using the first decoding unit, the first encoding information to obtain the first decoding information comprises:

performing, by using the $i^{th}$ connection-C after transforming the three-dimensional decoding information inputted from the first input terminal and the three-dimensional encoding information inputted from the second input terminal into the same three-dimensional space, weighted summation on the three-dimensional decoding information and the three-dimensional encoding information in the three-dimensional space; and providing the result of the weighted summation as the input of the $(i+1)^{th}$ decoding layer.

7. The method according to claim 6, wherein the second input terminal of the $i^{th}$ connection-C is further connected to an output terminal of the $(i+1)^{th}$ encoding layer in the first encoding unit through an $i^{th}$ connection-B, wherein the method of claim 6 further comprises converting, by the $i^{th}$ connection-B, two-dimensional encoding information outputted by the $(i+1)^{th}$ encoding layer into three-dimensional encoding information.

8. The method according to claim 7, further comprising expanding, by the $i^{th}$ connection-B, the two-dimensional encoding information outputted by the $(i+1)^{th}$ encoding layer into m layers in a vertical dimension, and determining expanded two-dimensional encoding information of m layers as the three-dimensional encoding information, m being a positive integer.

9. The method according to claim 3, wherein the fusion decoding unit comprises a neural network of n+2 fusion decoding layers, the n+2 fusion decoding layers comprising:

an up-sampling layer, n cascaded up-convolutional layers, and a three-dimensional convolutional layer, an output terminal of the up-sampling layer being connected to the first up-convolutional layer, the $n^{th}$ up-convolutional layer being connected to the three-dimensional convolutional layer, and n being a positive integer, wherein the fusion decoding unit further comprises a connection-C, a first input terminal of the connection-C being connected to an input terminal of the first decoding unit, a second input terminal of the connection-C being connected to an input terminal of the second decoding unit, and an output terminal of the connection-C being connected to an input terminal of the up-sampling layer, wherein the method according to claim 3 further comprises performing weighted summation, by the connection-C is used, on three-dimensional encoding information inputted from the first input terminal and three-dimensional encoding information inputted from the second input terminal, and using a result of the summation as an input of a next fusion decoding layer.

10. The method according to claim 1, further comprising training the generator based on a generative adversarial network by using a loss function of the generator comprising at least one of:
    an adversarial loss;
    the adversarial loss and a reconstruction loss;
    the adversarial loss and a projection loss; or
    the adversarial loss, the reconstruction loss, and the projection loss, wherein
    the adversarial loss is used for representing a semantic loss between the three-dimensional model reconstructed by the generator and a sample CT image, the reconstruction loss is used for representing a pixel-level discrepancy loss between the three-dimensional model reconstructed by the generator and the sample CT image, and the projection loss is used for representing a discrepancy loss between the three-dimensional model reconstructed by the generator and the sample CT image on at least one projection plane.

11. The method according to claim 10, further comprising:
    obtaining a training dataset, the training dataset comprising at least two training samples;
    setting a discriminator corresponding to the generator;
    fixing a first neural network parameter in the generator at an $i^{th}$ training stage, and optimizing a second neural network parameter in the discriminator by using a training sample in the training dataset;
    fixing the second neural network parameter in the discriminator at an $(i+1)^{th}$ training stage, and optimizing the first neural network parameter in the generator by using the other training sample in the training dataset; and
    performing the foregoing two training stages alternately, until the first neural network parameter and the second neural network parameter steadily converge.

12. The method according to claim 11, wherein obtaining the training dataset comprises:
    obtaining at least two real CT images;
    generating a corresponding first virtual X-ray image and a corresponding second virtual X-ray image for each of the at least two real CT images; and
    designating each of the at least two real CT images, the corresponding first virtual X-ray images, and the corresponding second virtual X-ray images as one of the at least two training samples.

13. A computer device, comprising a processor and a memory, the memory storing at least one program, the at least one program, when loaded and executed by the processor, being configured to perform the method of claim 1.

14. A non-transitory computer-readable storage medium, storing at least one program, the at least one program, when loaded and executed by a processor, being configured to perform the method of claim 1.

15. A three-dimensional image synthetic method, performed by a computer device, the method comprising:

obtaining a first cross-sectional image and a second cross-sectional image, the first cross-sectional image and the second cross-sectional image being images acquired for a target object from two orthogonal viewing angles;

obtaining an encoder and a decoder, the encoder comprising a first encoding unit and a second encoding unit, and the decoder comprising a first decoding unit, a second decoding unit, and a fusion decoding unit;

performing, by using the first encoding unit, two-dimensional encoding on the first cross-sectional image to obtain first encoding information;

decoding, by using the first decoding unit, the first encoding information to obtain first decoding information;

performing, by using the second encoding unit, two-dimensional encoding on the second cross-sectional image to obtain second encoding information;

decoding, by using the second decoding unit, the second encoding information, to obtain second decoding information; and performing, by using the fusion decoding unit, three-dimensional fusion by using the first decoding information and the second decoding information as data of different viewing angles in a three-dimensional space to obtain a three-dimensional image of the target object.

16. A three-dimensional image processing apparatus, comprising:
    an encoder, configured to perform, in parallel, two-dimensional encoding on a first cross-sectional image to obtain first encoding information and two-dimensional encoding on a second cross-sectional image to obtain second encoding information, the first cross-sectional image and the second cross-sectional image being images acquired for a target object from two orthogonal viewing angles; and
    a decoder in communication with the encoder and being configured to:
        decode, in parallel, the first encoding information to obtain first decoding information and the second encoding information to obtain second decoding information; and
        perform three-dimensional fusion by using the first decoding information and the second decoding information as data of different viewing angles in a three-dimensional space to obtain a three-dimensional image of the target object.

17. The three dimensional image processing apparatus of claim 16, wherein the encoder comprising a first encoding unit and a second encoding unit, configured to perform, in parallel, the two-dimensional encoding on the first cross-sectional image and the two-dimensional encoding on the second cross-sectional image, wherein the first encoding unit comprises a neural network of n+2 encoding layers, the n+2 encoding layers comprising:
    a two-dimensional convolutional layer, n cascaded densely-connected layer, and a pooling layer, the two-dimensional convolutional layer being connected to the first densely-connected layer, the $n^{th}$ densely-connected layer being connected to the pooling layer, and n being a positive integer.

18. The three dimensional image processing apparatus of claim 16, wherein the decoder comprises a first decoding unit and a second decoding unit, configured to decode, in parallel, the first encoding information and the second encoding information, wherein the first decoding unit comprises a neural network of n+2 decoding layers, the n+2 decoding layers comprising:

an up-sampling layer, n cascaded up-convolutional layers, and a three-dimensional convolutional layer, the up-sampling layer being connected to the first up-convolutional layer, the $n^{th}$ up-convolutional layer being connected to the three-dimensional convolutional layer, n being a positive integer.

19. The three dimensional image processing apparatus of claim 16, wherein the decoder comprises a fusion decoding unit, configured to perform the three-dimensional fusion, wherein the fusion decoding unit comprises a neural network of n+2 fusion decoding layers, the n+2 fusion decoding layers comprising:

an up-sampling layer, n cascaded up-convolutional layers, and a three-dimensional convolutional layer, an output terminal of the up-sampling layer being connected to the first up-convolutional layer, the $n^{th}$ up-convolutional layer being connected to the three-dimensional convolutional layer, and n being a positive integer.

20. The three dimensional image processing apparatus of claim 19, wherein the fusion decoding unit further comprises n compound connections-C, each of the compound connections-C comprising a first connection-C and a second connection-C, wherein a first input terminal of an $i^{th}$ first connection-C is connected to an output terminal of an $(i+1)^{th}$ decoding layer in the first decoding unit, a second input terminal of the $i^{th}$ first connection-C is connected to an output terminal of an $(i+1)^{th}$ decoding layer in the second decoding unit, an output terminal of the $i^{th}$ first connection-C is connected to a first input terminal of an $i^{th}$ second connection-C, a second input terminal of the $i^{th}$ second connection-C is connected to an output terminal of an $i^{th}$ fusion decoding layer in the fusion decoding unit, and an output terminal of the $i^{th}$ second connection-C is connected to an input terminal of an $(i+1)^{th}$ fusion decoding layer in the fusion decoding unit.

\* \* \* \* \*